(12) United States Patent  
Ueda et al.

(10) Patent No.: US 7,591,166 B2  
(45) Date of Patent: Sep. 22, 2009

(54) TACTILE SENSOR AND USE THEREOF

(75) Inventors: Jun Ueda, Ikoma (JP); Yutaka Ishida, Nara (JP); Tsukasa Ogasawara, Kyoto (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 134 days.

(21) Appl. No.: 11/662,657

(22) PCT Filed: Jun. 16, 2005

(86) PCT No.: PCT/JP2005/011075

§ 371 (c)(1),
(2), (4) Date: Nov. 21, 2007

(87) PCT Pub. No.: WO2006/030570

PCT Pub. Date: Mar. 23, 2006

(65) Prior Publication Data

US 2008/0202202 A1 Aug. 28, 2008

(30) Foreign Application Priority Data

Sep. 14, 2004 (JP) .............................. 2004-267382

(51) Int. Cl.
*G01N 3/56* (2006.01)
(52) U.S. Cl. ............................................. 73/9
(58) Field of Classification Search ................. 73/9
See application file for complete search history.

(56) References Cited

U.S. PATENT DOCUMENTS 5,501,097 A 3/1996 Nomura 5,967,990 A 10/1999 Thierman et al.
6,266,600 B1 * 7/2001 Miyazaki .......................... 73/9

FOREIGN PATENT DOCUMENTS

JP 7-151672 6/1995

(Continued)

OTHER PUBLICATIONS

Atsutoshi Ikeda et al., "Shoki Suberi Sensor O Mochiita Danseitai no Hajiryoku Seigyo", Dai 4 Kai System Integration Bumon Gakujutsu Koenkai, Dec. 19, 2003, pp. 424-425.

(Continued)

*Primary Examiner*—Hezron Williams
*Assistant Examiner*—Alex DeVito
(74) *Attorney, Agent, or Firm*—Harness, Dickey & Pierce, P.L.C.

(57) ABSTRACT

A tactile sensor of an embodiment of the present invention includes: a sensing section having an elastic member at a portion which contacts a measurement target; an image acquiring section for acquiring as image information the state of a contact surface of the measurement target and the elastic member, before and after application of an external force tangential to the contact surface; a deformation analyzing section for analyzing deformation information of the contact surface, based on the image information acquired by the image acquiring section; an external force detecting section for detecting the external force applied tangential to the contact surface; and an estimating section for estimating a slippage margin between the measurement target and the elastic member, based on (I) the deformation information of the contact surface, which information acquired by the deformation analyzing section, (II) the external force detected by the external force detecting section, and (III) an object constant of the elastic member. With this tactile sensor, slippage margin can be simply but accurately estimated.

18 Claims, 11 Drawing Sheets

FOREIGN PATENT DOCUMENTS

| | | |
|---|---|---|
| JP | 2001-21482 | 1/2001 |
| JP | 2003-127081 A | 5/2003 |
| JP | 2004-160614 A | 6/2004 |

OTHER PUBLICATIONS

Presentation at academic conference. "Grip force control of elastic body based on contact surgace eccentricity during incipient slip" (Lecture on Robotics and Mechatronics, 2004) Meijo University (Nagoya-shi, Aichi, Japan).

Presentation at academic conference. "Grip-force control of NAIST-Hand using slop margin feedback" (the 22nd Annual Conference of the Robotics Society of Japan) Gifu University (Gifu-shi, Gifu, Japan).

Takashi Kawai et al. "Development of Strain Distribution Sensor Having Curved Surface for Grip Force Control." The Japan Society of Mechanical Engineers, Collected Papers C Edition, vol. 64, No. 627, pp. 4264-4270, 1998.

Hideo Fujimoto et al. "Soft Finger Which Built in Tactile Sensor for Tele-grasping by Multi-fingered Hand." Lecture on Robotics and Mechatronics, 2P2-I01 2002.

* cited by examiner

TACTILE SENSOR AND USE THEREOF

TECHNICAL FIELD

The present invention relates to a tactile sensor and a use thereof. Particularly, the present invention relates to a tactile sensor and a use thereof, both of which are capable of simply but surely estimating a slippage margin, while avoiding an entire slippage.

BACKGROUND ART

It is known that the person only uses a grip force slightly larger than the minimum grip force to lift an object with his/her finger, even though the friction factor is unknown. To let a robot do this gripping motion, the robot needs to be provided with a tactile sensor capable of detecting a friction factor and/or a "slippage margin" indicating how easily a gripped object slips. There are following developments in regard to such a tactile sensor. One is a tactile sensor to be mounted in a fingertip of a robot. This tactile sensor senses a friction factor of a gripped object, by actually letting the object slip. Another development is a tactile sensor or a friction factor measuring device which detects vibration occurring at the beginning of slippage.

Specifically, for example, Non-Patent Document 1 discloses a pressure-sensing tactile sensor having silicon resin with a curved surface. Inside the silicon resin, a number of strain sensors are provided. This tactile sensor estimates a friction factor or the like, based on how the stress inside the sensor varies before the gripped object starts to slide. Another exemplary pressure-sensing tactile sensor is disclosed in Non-Patent Document 2. This document discloses a tactile sensor with a fingertip having a curved surface supported by plural springs. This tactile sensor estimates a friction factor or the like, based on how internal stress varies inside the sensor before the gripped object starts to slide.

Further, Patent Document 1 discloses a pressure-sensing tactile sensor which uses a hole and ultrasonic wave. The document describes a friction factor measuring method and a maximum transverse-displacement force measuring method as follows. Namely, in these methods, at the moment when the tactile sensor is pushed against a target, the tactile sensor observes the stress and a strain component in the direction along a surface of the target. In this manner, the friction factor and the maximum transverse-displacement force are stably detected.

Although Patent Document 2 discloses no pressure-sensing tactile sensor, it discloses an image processing algorithm as a technology relative to a tactile sensor. The document describes that a contact surface of a target and a transparent-gel-made sensing section of the sensor is observed by using a camera, and variation in the shape of the sensing section is estimated using the image processing algorithm, based on the obtained image information.

Further, Patent Document 3 discloses a portable friction gauge for estimating the friction factor as follows. A device for estimating the friction factor is placed on a floor face, and a force is increased little by little in the tangential direction to the device. Then based on a force at the time when there occurs slippage, the gauge of Patent Document 3 estimates the friction factor.

[Patent Document 1]

Japanese Unexamined Patent Publication No. 2001-021482 (Tokukai 2001-021482; Published on Jan. 26, 2001)

[Patent Document 2]

Specification of U.S. Pat. No. 5,967,990

[Patent Document 3]

Japanese Unexamined Patent Publication No. 1995-151672 (Tokukaihei 07-151672; Published on Jun. 16, 1995)

[Non-Patent Document 1]

Kawai Takashi and two others, "Development of Strain Distribution Sensor Having Curved Surface for Grip Force Control", The Japan Society of Mechanical Engineers, Collected Papers C Edition, Vol. 64, No. 627, pp. 4264-4270, 1998

[Non-Patent Document 2]

Fujimoto Hideo, Sano Akihito, Nishitsune Kai, Uehara Yusaku, "Tactile Sensor Mounted Soft Finger for Remote Gripping with a Multi-fingered Hand", Lecture on Robotics and Mechatronics, 2002

The above-mentioned pressure-sensing tactile sensors have the following problems. First, regarding the tactile sensor disclosed in Non-Patent Document 1, the number of strain sensors which can be provided in silicon resin is limited. Provision of tactile sensors needed for achieving sufficient detection sensibility increases the size of the device. On the other hand, downsizing of the device will cause insufficient detection accuracy.

Similarly, regarding the tactile sensor of Non-Patent Document 2, the number of springs which can be provided inside the sensor is limited. Therefore, sufficient detection accuracy is not obtained.

Further, in regard to the tactile sensor of Patent Document 1, the number of holes which can be provided in the sensor is limited. This causes a problem in the detection accuracy. Additionally, prior to the use of such a sensor, phase variation of the friction factor and ultrasonic wave needs to be measured a number of times to prepare a table that grasps the interrelation therebetween. This makes the use of the sensor extremely troublesome.

Further, although the technology of Patent Document 2 is relative to a tactile sensor, it is not relative to detection of a slippage margin or a friction factor. Therefore, measurement of the slippage margin, friction factor, or the like is not possible with the technology alone.

Further, in the measurement of the friction factor with the use of the portable friction gauge of Patent Document 3, it is necessary to cause an entire slippage state in which an object to be measured actually starts to slip. For this reason, measurement of the friction factor or the like with the portable friction gauge is not easy. Furthermore, since the object needs to be actually slid when using the portable friction gauge, the gauge is only usable for a plane having a certain degree of broadness. This is a problem in terms of general use.

As described above, the pressure-sensing tactile sensor requires a number of stress sensors to accurately detect the friction factor or slippage between a measurement target and the sensing section of the sensor. However, since the device size needs to be reduced, the number of stress sensors which can be provided is limited due to the space of the device. Therefore, sufficient detection accuracy is not obtained. Furthermore, there is development of a technology of detecting, with a use of a camera, variation in the contact surface of an elastic member and a rigid object. However, there is no technology to apply the technology to measurement of slippage and the friction factor between objects.

Under the circumstances, there has been a strong demand for a tactile sensor and a method of using the same, to solve the above problems and allow for easy but accurate measurement of a slippage margin or a friction factor between objects.

DISCLOSURE OF INVENTION

The present invention has been attained in view of the above problems, and an object of the present invention is to provide a tactile sensor and use of the same to allow for easy but accurate measurement of a slippage margin or a friction factor between objects.

The inventors of the present invention diligently worked to solve the foregoing problems and accomplished the present invention by finding that deformation of a contact surface of (a) a sensor sensing section of a sensor, which is realized by an elastic member, and (b) a measurement target is measured by using a small camera, and a slippage margin is calculated from deformation information of the contact surface, a signal of a force applied to the contact surface in a tangential direction, and an object constant of the elastic member, by using a predetermined calculation algorithm, so that it is possible to accurately estimate the slippage margin while actually avoiding an entire slippage even when a friction factor of the measurement target is unknown. The present invention has been completed on the basis of such a novel finding and encompasses the following industrially useful objects or methods.

(1) A tactile sensor including: sensing means having an elastic member at a portion which contacts a measurement target; image acquiring means which acquires as image information a state of the contact surface of (a) the measurement target and (b) the elastic member, before and after application of an external force tangential to the contact surface; deformation analyzing means which analyzes deformation information of the contact surface, based on the image information acquired by the image acquiring means; and estimating means which estimates a slippage margin between the measurement target and the elastic member, based on (I) the deformation information of the contact surface, which information acquired by the deformation analyzing means, (II) the external force applied tangential to the contact surface, and (III) an object constant of the elastic member.

(2) A tactile sensor including: sensing means having an elastic member at a portion which contacts a measurement target; image acquiring means which is set so that a central position of the contact surface is always in a predetermined position, before the external force is applied tangential to the contact surface of (a) the measurement target and (b) the elastic member, and acquires as image information a state of the contact surface after the external force is applied tangential to the contact surface under a condition where the image acquiring means is set as above; deformation analyzing means which analyzes deformation information of the contact surface, based on the image information acquired by the image acquiring means; and estimating means which estimates a slippage margin between the measurement target and the elastic member, based on (I) the deformation information of the contact surface, which information acquired by the deformation analyzing means, (II) the external force applied tangential to the contact surface, and (III) an object constant of the elastic member.

(3) The tactile sensor according to (1) or (2), further including: external force detecting means which detects the external force applied tangential to the contact surface.

(4) The tactile sensor according to any one of (1) through (3), wherein the elastic member is substantially in such a hemispherical shape that its circumferential part contacts the measurement target, the deformation analyzing means includes: a radius calculating section which calculates, based on the image information acquired by the image acquiring means, a radius of the contact surface; and a relative displacement calculating section which calculates, based on the image information acquired by the image acquiring means, a relative displacement of the contact surface, which displacement occurs when the external force is applied tangential to the contact surface, and the estimating means estimates the slippage margin by using a calculating formula of assumed Hertz Contact, based on the radius of the contact surface and the relative displacement, each acquired by the deformation analyzing means, the external force detected by the external force detecting means, and the object constant of the elastic member.

(5) The tactile sensor according to any one of (1) through (4), wherein a characteristic diagram is formed on a surface of the elastic member, the characteristic diagram allowing the image acquiring means to clearly recognize the central position of the contact surface in a state before the external force is applied tangential to the contact surface.

(6) The tactile sensor according to any one of (1) through (5), wherein the elastic member is transparent, and the image acquiring means is provided on a back surface side of the elastic member which side is opposite to a surface which contacts the measurement target.

(7) The tactile sensor according to any one of (1) through (6), further including: friction factor estimating means which estimates a friction factor between the measurement target and the elastic member, based on the slippage margin estimated by the estimating means.

(8) A friction inspecting device including a tactile sensor according to any one of (1) through (7).

(9) The friction inspecting device according to (8), wherein the tactile sensor is mounted on a tubiform enclosure so that the elastic member of the tactile sensor is allowed to contact an inspection target.

(10) A gripping device comprising a tactile sensor according to any one of (1) through (7).

(11) The gripping device according to (10), including: control means which controls a grip force so as to maintain a predetermined slippage margin when an elastic member of the tactile sensor mounted to the gripping device comes into contact with a gripping target to grip the gripping target, by increasing the grip force when the slippage margin of the contact surface of (A) the elastic member of the tactile sensor and (B) the gripping target decreases, and decreasing the grip force when the slippage margin of the contact surface of (A) the elastic member of the tactile sensor and (B) the gripping target increases.

(12) The gripping device according to (10) or (11) wherein the gripping device is a robot hand.

(13) A slippage margin measuring method including: a contacting step of causing an elastic member to contact a measurement target; a first image acquiring step of acquiring as image information a state of a contact surface of (a) the measurement target and (b) the elastic member in the contacting step; an external force applying step of applying an external force tangential to the contact surface; a second image acquiring step of acquiring as image information a state of deformation which occurs on the contact surface due to the external force, applied in the external force applying step; a deformation analyzing step of analyzing deformation information of the contact surface, based on the image information acquired in the first image acquiring step and the second image acquiring step; and an estimating step of estimating a slippage margin between the measurement target and the elastic member, based on (I) the deformation information of the contact surface, which information acquired in the deformation analyzing step, (II) the external force applied in the external force applying step, and (III) an object constant of the elastic member.

(14) The slippage margin measuring method according to (13), wherein the elastic member is substantially in such a hemispherical shape that its circumferential part contacts the measurement target, the deformation analyzing step comprises: a radius calculating step of calculating, based on the image information acquired in the first image acquiring step and/or second image acquiring step, a radius of the contact surface of (a) the measurement target and (b) the elastic member; and a relative displacement calculating step of calculating, based on the image information acquired in the first image acquiring step and/or second image acquiring step, a relative displacement of the contact surface of (a) the measurement target and (b) the elastic member, when a force is applied to the elastic member in a tangential direction to the contact surface of (a) the measurement target and (b) the elastic member, and the estimating step is a step of estimating the slippage margin by using a calculating formula of assumed Hertz Contact, based on the radius of the contact surface and the relative displacement, each acquired in the deformation analyzing step, the external force applied in the external force applying step, and the object constant of the elastic member.

(15) A slippage margin measuring method including: a contacting step of causing an elastic member to contact a measurement target; an external force applying step of applying an external force tangential to the contact surface; an image acquiring step of acquiring as image information a state of deformation which occurs on the contact surface due to the external force applied in the external force applying step; a deformation analyzing step of analyzing deformation information of the contact surface, based on the image information acquired in the image acquiring step; and an estimating step of estimating a slippage margin between the measurement target and the elastic member, based on (I) the deformation information of the contact surface, which information acquired in the deformation analyzing step, (II) the external force applied in the external force applying step, and (III) an object constant of the elastic member, wherein the image acquiring step is a step of using image acquiring means which is set so that a central position of the contact surface is always in a predetermined position, before the external force is applied tangential to the contact surface of (a) the measurement target and (b) the elastic member, and acquires as image information a state of the contact surface after the external force is applied tangential to the contact surface under a condition where the image acquiring means is set as above.

(16) The slippage margin measuring method according to (15), wherein the elastic member is substantially in such a hemispherical shape that its circumferential part contacts the measurement target, the deformation analyzing step comprises: a radius calculating step of calculating, based on the image information acquired in the image acquiring step, a radius of the contact surface of (a) the measurement target and (b) the elastic member; and a relative displacement calculating step of calculating, based on (i) the image information acquired in the image acquiring step and (ii) pre-set coordinate information of the central position on the contact surface before the external force is applied, a relative displacement of the contact surface of (a) the measurement target and the (b) the elastic member, when a force is applied to the elastic member in a tangential direction to the contact surface of (a) the measurement target and (b) the elastic member, and the estimating step is a step of estimating the slippage margin by using a calculating formula of assumed Hertz Contact, based on the radius of the contact surface and the relative displacement, each acquired in the deformation analyzing step, the external force applied in the external force applying step, and the object constant of the elastic member.

(17) The slippage margin measuring method according to any one of (13) through (16), further including: an external force detecting step of detecting an external force applied in the external force applying step, wherein in the estimating step, an external force detected in the external force detected in the external force detecting step is used as an external force that has been applied in the external force applying step.

(18) The slippage margin measuring method according to any one of (13) through (17), wherein the elastic member is transparent, and the image acquiring step is a step of acquiring image information by using image acquiring means that is provided on a back surface side of the elastic member which side is opposite to a surface which contacts the measurement target.

Note that the deformation analyzing means and estimating means both provided in the tactile sensor and the control means provided in the gripping device may be realized by a computer. In this case, the scope of the present invention includes a tactile sensor, a gripping device control program, and a computer-readable storage medium storing the control program, all of which realizes the tactile sensor and the gripping device by means of a computer by causing the computer to function as the foregoing means.

BRIEF DESCRIPTION OF DRAWINGS

FIG. 2(*b*) is a diagram schematically showing a state where an external force $f_1$ is applied in a tangential direction while the elastic member and the measurement target are in contact with each other.

FIG. 5(*b*) is an explanatory diagram showing another specific method of calculation of a relative displacement, which calculation is performed by the relative displacement detecting section, in the present embodiment.

BEST MODE FOR CARRYING OUT THE INVENTION

The present invention is related to a tactile sensor capable of simply but accurately estimating slippage margin without causing an entire slippage, and also relates to a use of such a tactile sensor. In the following embodiment, a tactile sensor of the present invention is first described. After that, a friction inspecting device and a gripping device such as a robot hand or the like are described as a form of utilizing the tactile sensor.

<1. Tactile Sensor of the Present Invention>

In the present invention, specific structure, material, size and the like of a tactile sensor are not particularly limited, provided that the tactile sensor of the present invention includes at least: sensing means; an image acquiring section; a deformation analyzing section; and an estimating means. In other words, the structure of a widely-known conventional tactile sensor can be suitably used, except for the above described characteristic structures. It is preferable that the tactile sensor of the present invention further includes an external force detecting means. This external force detecting means is preferably provided if the later mentioned "external force" is a variable. However, the external force detecting means is not particularly needed if the information of "external force" is easily attainable without a need of detection (e.g., if the external force is settable as a constant value, or if the external force can be measured afterward). The following describes in detail an exemplary tactile sensor of the present invention having the external force detecting means.

Embodiment 1

Figure 1:
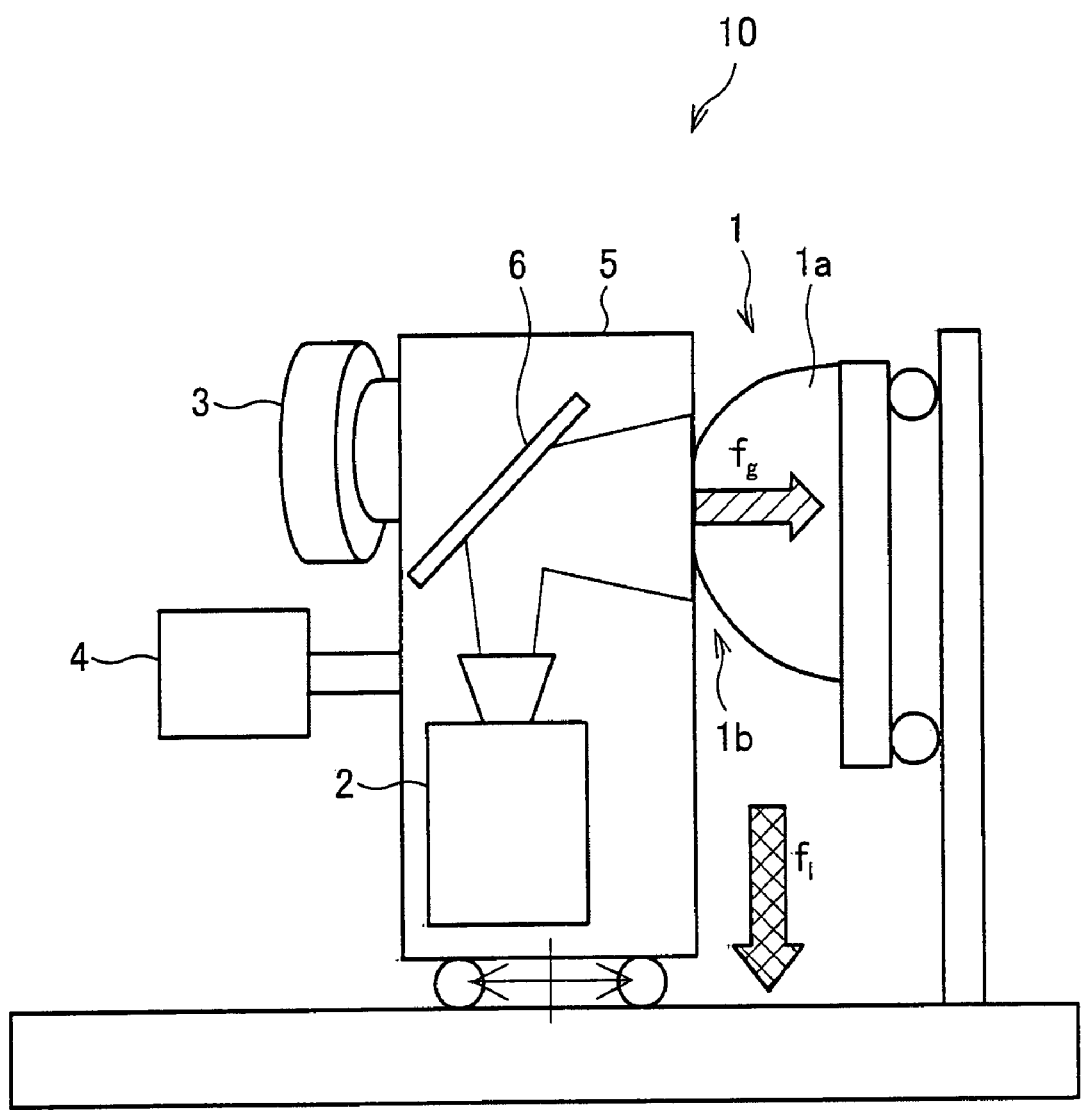
FIG. 1 is a diagram schematically showing a structure of a tactile sensor according to one embodiment of the present invention.

FIG. 1 is a schematic diagram illustrating the structure of a tactile sensor according to an embodiment of the present invention. As shown in FIG. 1, the tactile sensor 10 of the present embodiment includes: a sensing section 1; an image acquiring section 2; an external force detecting section 3; and an information processing unit 4. This tactile sensor 10 measures a slippage margin between a measurement target 5 and the sensing section 1.

The sensing section 1 functions as sensing means, and its structure and the like are not particularly limited as long as the sensing section 1 is provided with an elastic member 1a at a portion which contacts the measurement target 5. Here, the description reading "elastic member provided at a portion which contacts the measurement target" does not particularly limit the portion to provide the elastic member to a specific portion, as long as the elastic member is provided in a portion of the sensing means which portion contacts a measurement target subject to the measurement of slippage margin or the like. For example, the elastic member 1a is preferably provided at the leading end of the sensing section 1.

The "elastic member" deforms itself when contacting the measurement target 5 while causing no deformation of the measurement target 5. For example, the elastic member may be made of gel, rubber, or the like made of silicon resin, urethane resin, or the like.

Further, the shape, material, rigidity, and the like of the "measurement target (measurement target substance)" are not particularly limited, as long as the tactile sensor 10 is able to measure the slippage margin. However, it is preferable that the measurement target be a rigid body made of a material such as various metals, glass, or the like.

Further, the elastic member 1a is substantially in such a hemispherical shape that its circumferential part contacts the measurement target 5. This shape of the elastic member 1a allows for suitable utilization of the findings related to "Hertz Contact" (See Tribology Handbook, Japanese Society of Tribologists, Yokendo, 2001, pp. 7-25), and allows for accurate calculation of slippage margin or the like. In other words, the shape of the elastic member 1a is preferably such that the contact surface 1b formed when contacting the measurement target 5 is substantially in a circular shape.

Further, for an easier observation of deformation at the time of contact with the measurement target 5, a characteristic diagram is preferably formed in a region of the surface of the elastic member 1a which region corresponds to the contact surface 1b of the elastic member 1a and the measurement target 5. For example, as shown in later-described FIG. 3, the characteristic diagram may be a diagram which allows the image acquiring section 2 (described later) to clearly recognize the central position 1c of the contact surface 1b. More specifically, the characteristic diagram may be a marking (solid black dot in FIG. 3) at the central position of the contact surface 1b. With the characteristic diagram, deformation information (relative displacement δ) of the contact surface is accurately obtained as image information by the later-described image acquiring section 2. Note that the characteristic diagram is not limited to a solid black dot, as long as the characteristic diagram clearly indicates the central position. For example, the characteristic diagram may be a marking such as "X (cross)" or the like.

The image acquiring section 2, serving as image acquiring means, is not particularly limited, as long as it acquires as image information the states of the contact surface 1b of the elastic member 1a and the measurement target 5, before and after application of an external force tangential to the contact surface 1b of the measurement target 5 and the elastic member 1a. More specifically, the image acquiring section 2 is not particularly limited, provided that it performs the following steps: (I) a first image acquiring step of acquiring as the image information the state of the contact surface 1b when the measurement target 5 and the elastic member 1a contact each other; and (II) a second image acquiring step of acquiring as image information the state of deformation which occurs on the contact surface due to application of an external force tangential to the contact surface 1b.

No particular limitation is imposed regarding the images before and after application of an external force tangential to the contact surface 1b, which images are acquired by the image acquiring section 2 in the first and second image acquiring steps, meaning that the image acquiring section 2 may acquire the images in the form of separate static images or sequential images (moving image). However, the moving image is preferable. This is because, with the moving image, it is possible to detect the slippage margin of an arbitrary time by using the image information of the corresponding time, and to sequentially (continuously) estimate the slippage margin. For example, a solid imaging element such as a small camera or a CCD camera is suitably used as the image acquiring section 2.

Further, in the present embodiment, the measurement target 5 is transparent. The image acquiring section 2 is provided so that the image information of the contact surface 1*b* of the measurement target 5 and the elastic member 1 is acquired by observing, via a mirror 6, the contact surface 1*b* from the side of the measurement target 5 (through the measurement target 5). For acquiring a vivid image, illuminating means such as an LED may be used to illuminate an area nearby the contact surface 1*b*.

The external force detecting section 3, serving as the external force detecting means, detects an external force (shown by arrow $f_1$ in FIG. 1) applied tangential to the contact surface 1*b*. The external force detecting section 3, which is not particularly limited, can be suitably a conventionally-known stress sensor. For example, a six-axis force sensor or the like can be used. Note that the external force detecting section 3 may be one capable of detecting an external force (shown by arrow $f_g$ in FIG. 1) applied normal to the contact surface 1*b* of the measurement target 5 and the elastic member 1*a*.

Here, as is described later, it is preferable that the "external force" be a force that causes a local elastic deformation nearby the contact surface 1*b* and a minute slippage during an initial slippage. In other words, the external force is preferably a force that does not cause entire slippage (i.e., a force such that the gripped object does not start to slide entirely).

As mentioned above, an arrangement of a tactile sensor in which the external force detecting section 3 is not provided is also possible, in which arrangement information of an external force applied tangential to the contact surface 1*b* is input beforehand or afterward via an input device (not shown), so that later-described predetermined calculation process can be carried out. However, it is preferable to provide the external force detecting section 3 on the ground that it can accurately detect the "external force" applied tangential to the contact surface 1*b*.

The information processing unit 4 performs various kinds of information processing for the tactile sensor 10 to estimate the slippage margin. The information processing unit 4 includes a deformation analyzing section 7 and an estimating section 8. The deformation analyzing section 7 serves as deformation analyzing means which analyzes deformation information of the contact surface 1*b* of the measurement target 5 and the elastic member 1*a*, based on the image information acquired by the image acquiring section 2. The estimating section 8 serves as estimating means which estimates the slippage margin between the measurement target 5 and the elastic member 1*a*, based on: the deformation information of the contact surface acquired by the deformation analyzing section 7; the external force detected by the external force detecting section 3; and an object constant of the elastic member 1*a*.

Before proceeding to the description on the function and operation of the information processing unit 4 which is the characteristic part of the tactile sensor 10 of the present embodiment, the following provides description in regard to a contact state in which the elastic member 1*a* and the measurement target 5 of the present embodiment contact each other.

Figure 2:
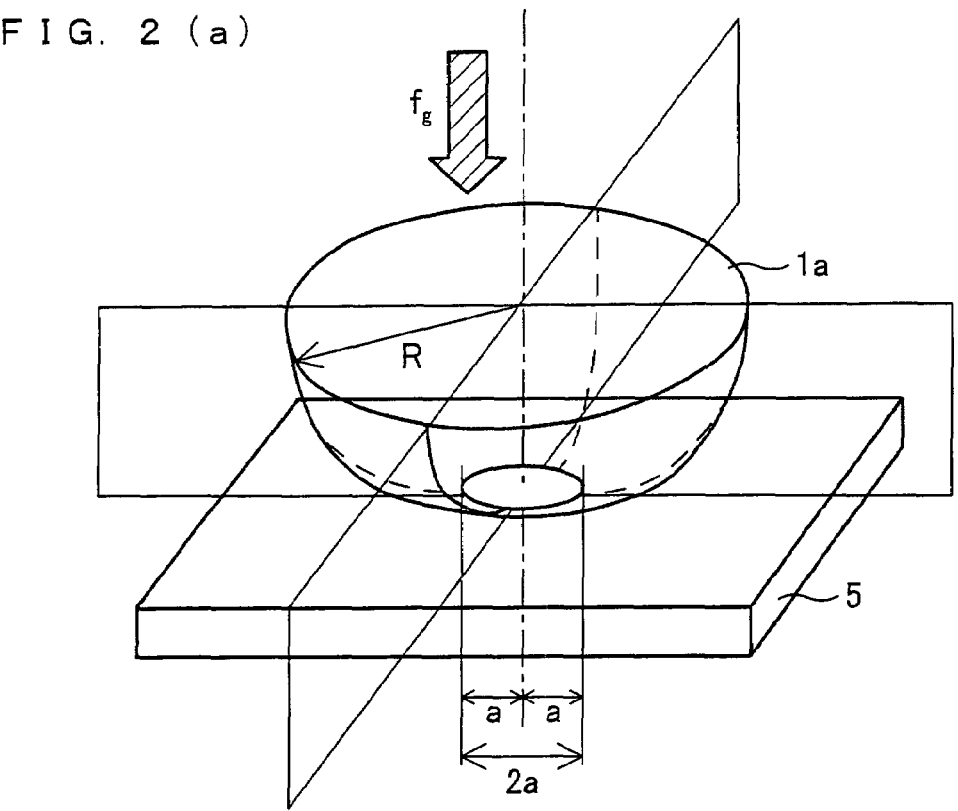
FIG. 2(*a*) is a diagram schematically showing a state where an elastic member and a measurement target are in contact with each other in the embodiment of the present embodiment.
Figure 2:
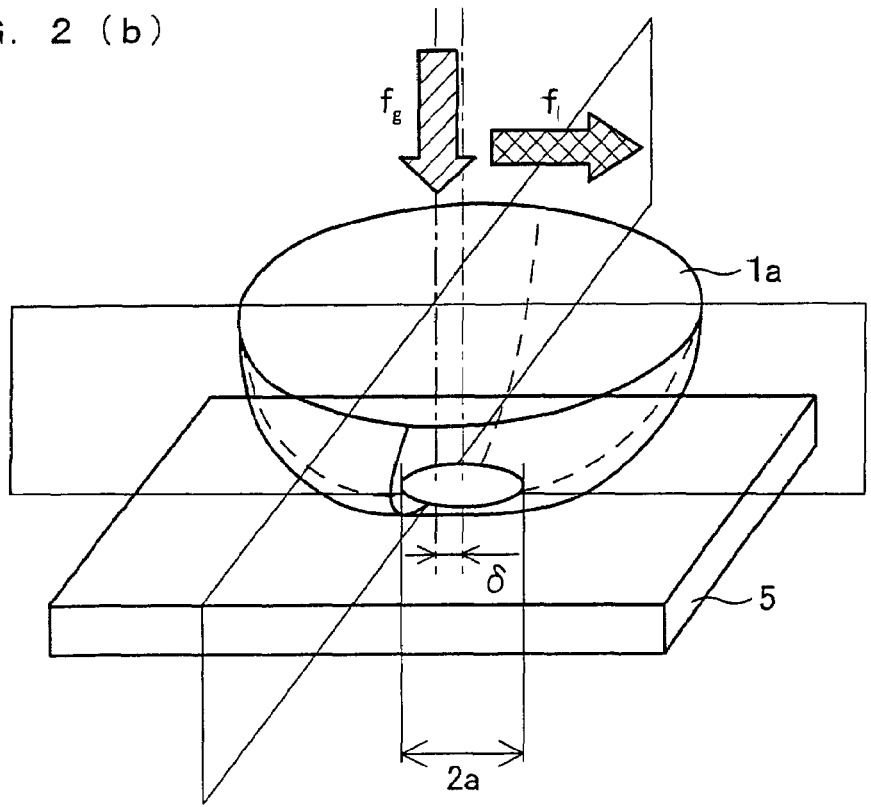

FIG. 2(*a*) is a diagram schematically illustrating a state in which the elastic member 1*a* and the measurement target 5 of the present embodiment are in contact with each other. FIG. 2(*b*) is a diagram schematically illustrating a state in which an external force $f_1$ is applied in tangential direction, while the elastic member 1*a* and the measurement target 5 are in contact with each other. This contact of the hemispherical elastic member 1*a* and the measurement target 5 (flat rigid plate) is called Hertz contact, and various analyses were conducted (See Tribology Handbook, Japanese Society of Tribologists, Yokendo, 2001, pp. 7-25).

The hemispherical elastic member 1*a* whose radius is R and the rigid plane form a circular contact surface 1*b* as shown in FIG. 2(*a*), and the radius a of the circular contact surface 1*a* is given by the following formula (1):

$$a = \left(\frac{3f_g R}{2E'}\right)^{1/3}. \tag{1}$$

In the contact of the elastic member 1*a* and the measurement target (flat rigid plate) 5, the contact force normal to the contact surface is weaker in the circumferential portion than it is in the central portion of a contact region. Under this condition, the restraint in the circumferential portion is weak. Accordingly, when a load force in the tangential direction is applied, slippage occurs earlier in the circumferential portion than in the central portion. This local slippage occurring within the contact surface 1*b* is hereinafter referred to as initial slippage. Assuming that a Stick Region is a region where no slippage occurs, and that a Slip Region is a region where a slippage occurs, the Stick Region is a circular region whose radius c from the center of the contact is given by: Radius $c = a(1-\Phi)^{1/3}$. $\Phi$ is a tangential modulus, and is given by $\Phi = f_1/\mu f_g$. $f_1$ is a load force (external force) applied in the tangential direction, and $\mu$ is a factor of friction which acts on the contact surface 1*b*. Application of the above-described force to the elastic member 1*a* in the tangential direction causes a minute slippage due to local elastic deformation nearby the contact surface 1*b* and the initial slippage. This minute slippage causes a relative displacement $\delta$ as shown in FIG. 2.

Figure 3:
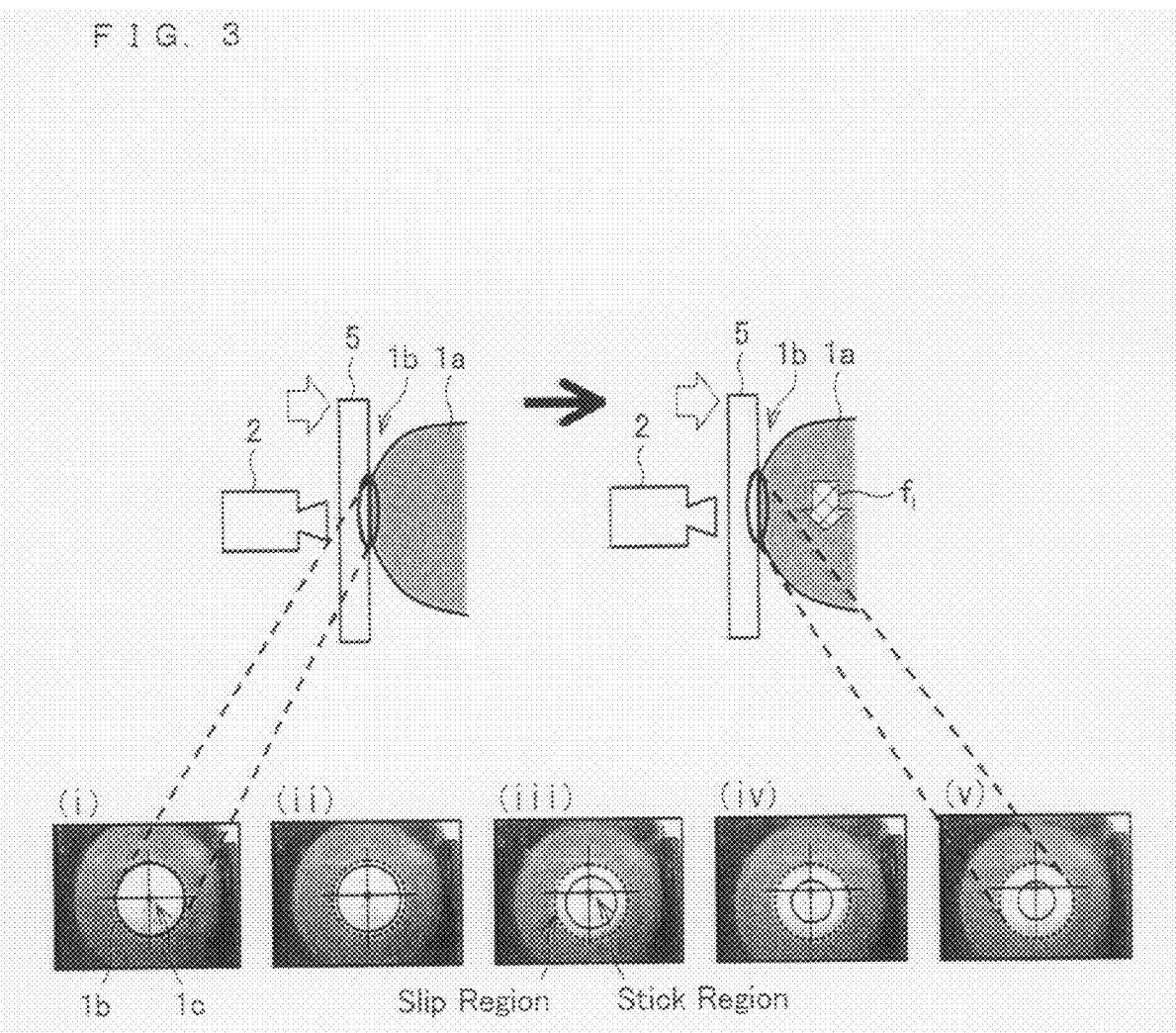
FIG. 3 is a diagram schematically showing a situation where the external force $f_1$ is applied while the measurement target and the elastic member are in contact with each other in the present embodiment, and also presents states of deformation on the contact surface, which states are acquired in the form of image information by an image acquiring section.

FIG. 3 is an experimental presentation of the above-described phenomenon. FIG. 3 schematically illustrates a situation where an external force $f_1$ is applied while the measurement target 5 and the elastic member 1*a* are in contact with each other. FIG. 3 also contains views obtained as image information by the image acquiring section 2, each showing deformation occurring on the contact surface 1*b* under such a situation. In each of the images (i) to (v), the portion looking white is the contact surface 1*b*, the black dot 1*c* is the central position of the contact surface, and the cross mark traces movement of the black dot. The region surrounded by a solid line is the Stick Region, and the region surrounded by the dotted line is the contact surface. The region between the dotted line and the solid line is the Slip Region. Further, the image (i) shows a state when the external force $f_1$ is not yet applied, and each of the images (ii) to (v) shows states after the external force $f_1$ is applied.

As illustrated in FIG. 3, when the external force (load force) $f_1$ is applied in the tangential direction, a slippage occurs (initial slippage) in the circumferential portion earlier than in the central portion, due to the weak restraint of the circumferential portion. Then, while the external force $f_1$ in the tangential direction is applied to the elastic member 1*a* as already mentioned, the central position (position of the black dot) 1*c* of the contact surface 1*b* moves as illustrated in FIG. 3, due to the minute slippage caused by the local elastic deformation nearby the contact surface 1*b* and the initial slippage. As a result, a relative displacement δ occurs. The relative displacement δ is given by the following formula (2):

$$\delta = \frac{3\mu f_g}{16a}\left(\frac{2-\nu}{G}\right)\{1-(1-\Phi^{2/3})\}. \tag{2}$$

Here, $G=E/\{2(1+\nu)\}$, where: E is Young's modulus of the material of the elastic member 1a; and ν is the Poisson ratio of the material of the elastic member 1a. With these formulas, it is possible to acquire: a state of the contact surface 1b of the elastic member 1a and the measurement target 5; distribution of stress which acts on the contact surface 1b; and the relative displacement δ of the elastic member 1a.

Further, the slippage margin at the time of initial slippage is estimated as follows. Specifically, in a case of gripping the measurement target 5 while avoiding the slippage between the measurement target 5 and the elastic member 1a, as is done by human fingers, slippage margin w=1−Φ is used as the index for determining the grip force $f_g$ corresponding to the load force $f_1$. This slippage margin w is a dimensionless quantity which varies within a range of 0≦w≦1. While w=1, the elastic member 1a and the measurement target 5 are entirely in the Stick State. This state however transits into the initial slippage state, with decrease in the value of w, and the entire slippage state occurs when w=0.

Applying the above-mentioned Formula (2), Φ representing the slippage margin can be estimated. As already mentioned, G is given by Young's modulus E and Poisson ratio ν of the material of the elastic member 1a. Both G and ν are inherent constants (object constants) of the material of the elastic member 1a. Accordingly, variables needed for estimating Φ are: relative displacement δ; friction factor μ; grip force $f_g$; and radius a of the contact surface 1b. In the present embodiment, the contact surface 1b is observed by the image acquiring section 2 as already mentioned. Therefore, the relative displacement δ and the radius a can be calculated from the image information. Further, the grip force $f_g$ is the output of the gripper itself, and therefore is a known value. However, since the friction factor μ is unknown in the present embodiment, the both sides of the above formula (2) is divided by $f_1$, and the entire formula is expressed by using Φ only. As a result, the following secondary formula (3) regarding Φ is acquired.

$$\alpha^3\Phi^2(1-3\alpha^2)\Phi+(3\alpha-2)=0 \tag{3}$$

Here, α is given by the following formula (4), and is defined by the observed quantity and the object constants of the elastic member 1a.

$$\alpha = \frac{16Ga\delta}{(6-3\nu)f_t} \tag{4}$$

Thus, Φ is estimated as is shown by the following Formula (5):

$$\Phi = \frac{-(1-3\alpha^2) - \sqrt{(1-3\alpha^3)^2 - 4\alpha^3(3\alpha-2)}}{2\alpha^3} \tag{5}$$

As described, to acquire the slippage margin w=1−Φ between the elastic member 1a and the measurement target 5, it is only required to know the following information: the radius a of the contact surface 1b of the elastic member 1a and the measurement target 5; the external force $f_1$ applied to the elastic member 1a in the tangential direction; the relative displacement δ of the contact surface 1b occurring at the time of applying the external force $f_1$ to the elastic member 1a; and G and ν which are the object constants of the elastic member 1a. Amongst those, what needs to be actually measured are: radius a; external force $f_1$; and the relative displacement δ. As already mentioned, the external force $f_1$ is detected by the external force detecting section 3. Accordingly, the information processing unit 4 needs to calculate the radius a and the relative displacement δ, and to calculate the slippage margin at the end. On the basis of the above understandings, structures, functions, and operations of functional blocks constituting the information processing unit 4 are described below.

Figure 4:
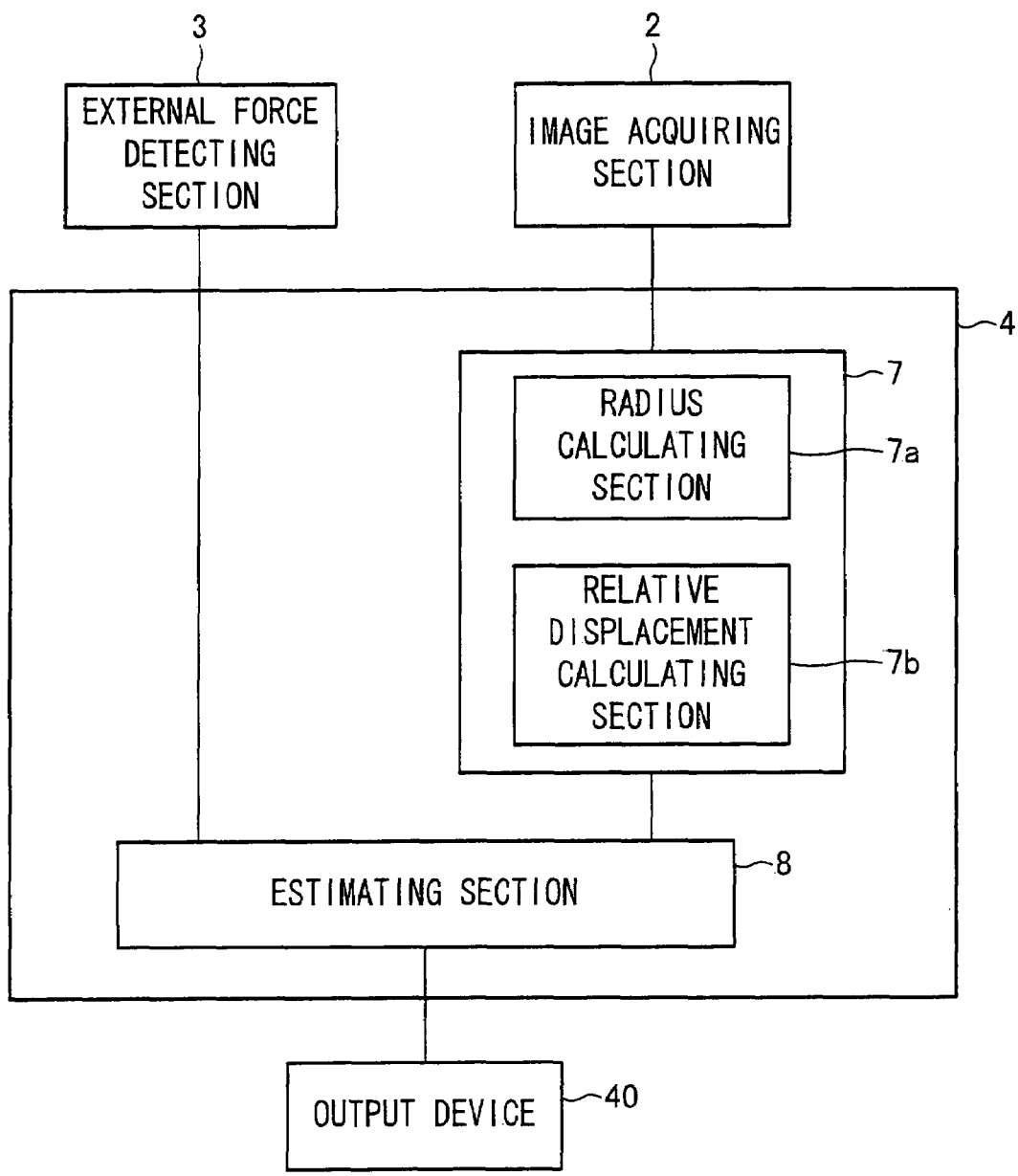
FIG. 4 is a diagram schematically showing functional blocks of the image acquiring section, an external force detecting section, and an information processing unit.

FIG. 4 is a diagram schematically illustrating functional blocks of the image acquiring section 2, the external force detecting section 3, and the information processing unit 4.

The deformation analyzing section 7 includes a radius calculating section 7a which calculates, based on the image information acquired by the image acquiring section 2, the radius a of the contact surface 1b of the measurement target 5 and the elastic member 1a. The deformation analyzing section 7 further includes a relative displacement calculating section 7b. The relative displacement calculating section 7b calculates, based on the image information acquired by the image acquiring section 2, the relative displacement 5 of the contact surface 1b of the measurement target 5 and the elastic member 1a, which displacement occurs when the external force $f_1$ tangential to the contact surface 1b is applied to the elastic member 1a.

In sum, the radius calculating section 7a performs a radius calculating step which calculates the radius a of the contact surface 1b of the measurement target 5 and the elastic member 1a, based on the image information acquired in the first image acquiring step and/or the second image acquiring step. Further, the relative displacement calculating section 7b performs a relative displacement calculating step of calculating, based on the image information acquired in the first image acquiring step and/or the second image acquiring step, the relative displacement δ of the contact surface 1b of the measurement target 5 and the elastic member 1a, which displacement occurs when a force tangential to the contact surface 1b is applied to the elastic member 1a.

In the calculation of the radius a performed by the radius calculating section 7a, for example, the radius a may be acquired by directly measuring the radius of a substantially circular contact surface on the basis of the image information. Specifically, the radius calculating section 7a is capable of acquiring the radius a by calculating, based on the image information of the contact surface 1b before the application of an external force $f_1$ to the contact surface 1b in the tangential direction, the distance between the central point 1c of the contact surface 1b and the periphery of the contact surface. Alternatively, assuming that the contact surface 1b is substantially in circular shape, the radius a can be given by $a=(S/\pi)^{1/2}$, where S is the gross area of the contact surface 1b. In this case, there is no need for acquiring the central position 1c from the image of the contact surface 1b before the application of the external force $f_1$.

Further, the central position 1c can be a position of a barycenter of the contact surface 1b, which barycenter is obtained by calculation.

Further, for example, in the calculation of the relative displacement δ performed by the relative displacement calculating section 7b, it is possible to acquire, based on the image information, the relative displacement δ of the contact surface 1b of the measurement target 5 and the elastic member 1a.

This is described more specifically, in reference to the panels (i) to (v) of FIG. 3. Using the image information of the contact surface 1b before and after the application of the external force $f_1$ in the tangential direction, the central position 1c is compared between these pieces of image information. Then, the relative displacement δ is calculated as the amount (variation amount) the central position 1c has traveled.

Figure 5:
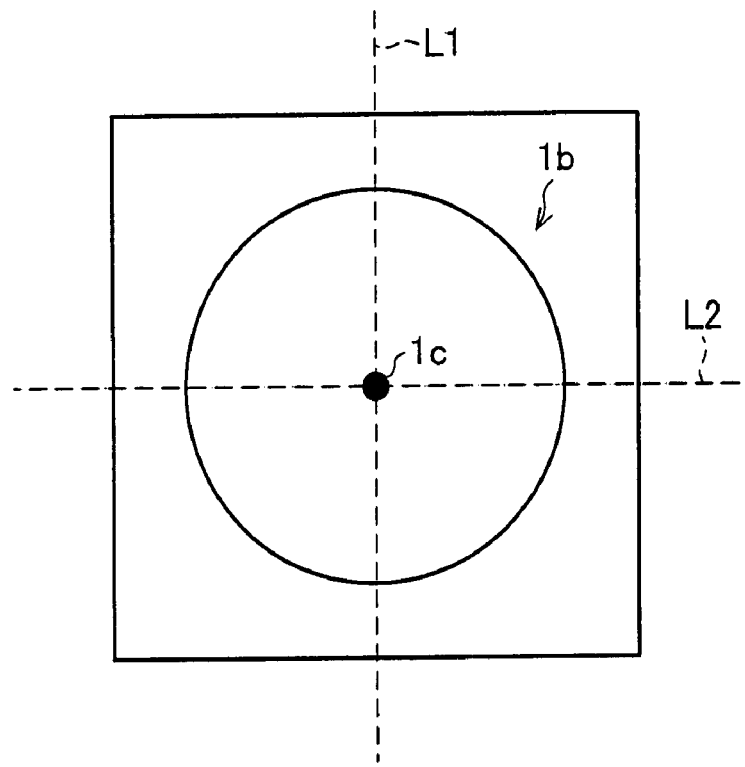
FIG. 5(*a*) is an explanatory diagram showing a specific method of calculation of a relative displacement, which calculation is performed by a relative displacement detecting section, in the present embodiment.
Figure 5:
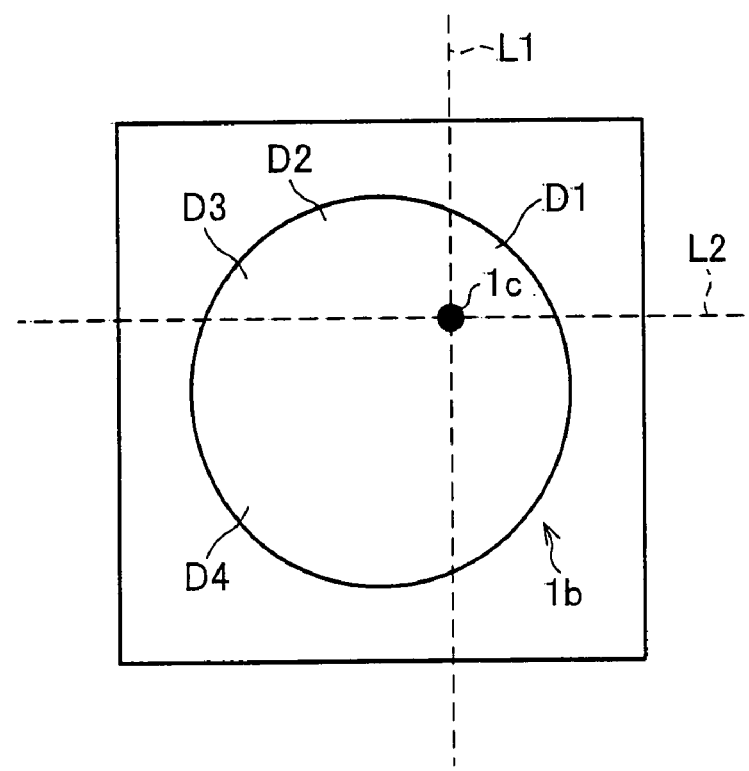

For example, as shown in FIG. 5, the travel amount of the central position 1c is calculated as follows, from the difference value of areas. FIG. 5(a) is a diagram schematically illustrating the image information of the contact surface 1b before the application of the external force $f_1$ in the tangential direction. FIG. 5(b) is a diagram schematically illustrating the image information of the contact surface 1b after the application of the external force $f_1$ in the tangential direction.

First, as illustrated in FIG. 5(b), the relative displacement calculating section 7b divides a contact surface region in an acquired image into regions D1 and D2, by a straight line L1 longitudinally running through the central position 1c of the contact surface 1b. Next, the relative displacement calculating section 7b calculates the respective areas S1 and S2 of the regions D1 and D2, and calculates the difference value ΔS1 (=S2−S1) of the areas of the regions D1 and D2.

Then, from the difference value ΔS1, the relative displacement calculating section 7b calculates a travel amount ΔX of the central position 1c, where the travel amount ΔX is the amount of the central position 1c traveled along the X-axis from the central position 1c in the image information (FIG. 5(a)) of the contact surface 1b before the external force $f_1$ is applied in the tangential direction. For example, the travel amount ΔX may be calculated by multiplying the difference value ΔS1 by a conversion factor derived from the relation between (I) a size in the lateral direction of a display screen for displaying the image information, and (II) a size in the lateral direction of the contact surface 1b. Alternatively, the travel amount ΔX may be calculated by substituting the difference value ΔS1 into a conversion function derived from the relation between (I) a size in the lateral direction of a display screen for displaying the image information, and (II) a size in the lateral direction of the contact surface 1b.

Next, the relative displacement calculating section 7b divides the acquired image of the contact surface region into regions D3 and D4, by a lateral straight line L2 running through the central position 1c of the contact surface 1b. Then, the relative displacement calculating section 7b calculates the respective areas S3 and S4 of the regions D3 and D4, and calculates the difference value ΔS2 (=S4−S3) of the areas of the regions D3 and D4.

Next, from the difference value ΔS2, the relative displacement calculating section 7b calculates a travel amount ΔY of the central position 1c, where the travel amount ΔY is an amount the central position 1c traveled along the Y-axis from the central position 1c in the image information (FIG. 5(a)) of the contact surface 1b before the external force $f_1$ in the tangential direction is applied. The travel amount ΔY is calculated by using a conversion factor or a conversion function as in the case of the travel amount ΔX.

The X and Y coordinates of the central position 1c in the image information (FIG. 5(a)) of the contact surface 1b before the application of the external force $f_1$ in the tangential direction are calculated from, for example, the image information acquired in the first image acquiring step.

The estimating section 8 performs an estimating step of estimating the slippage margin. In the estimating step, the slippage margin is estimated by using a calculating formula of assumed Hertz Contact, based on the radius a of the contact surface 1b and the relative displacement δ, each acquired by the deformation analyzing section 7; the external force $f_1$ detected by the external force detecting section 3; and the object constants G and ν of the elastic member 1a. In other words, using aforementioned Formula (5), the estimating section 8 calculates Φ, and estimates the slippage margin w given by (1−Φ). The object constants G and ν of the elastic member 1a are inherent values of the elastic member 1a. Therefore, these values can be input in the estimating section 3 in advance. Alternatively, the values may be separately input every time the measurement is conducted.

Although no illustration is provided in the present embodiment, the tactile sensor 10 may include a friction factor estimating section which functions as friction factor estimating means which estimates the friction factor μ between the measurement target 5 and the elastic member 1a, based on the slippage margin estimated by the estimating section 8. With Φ having estimated by the above Formula (5), the friction factor is easily given by $\Phi = f_1/\mu f_g$.

Figure 6:
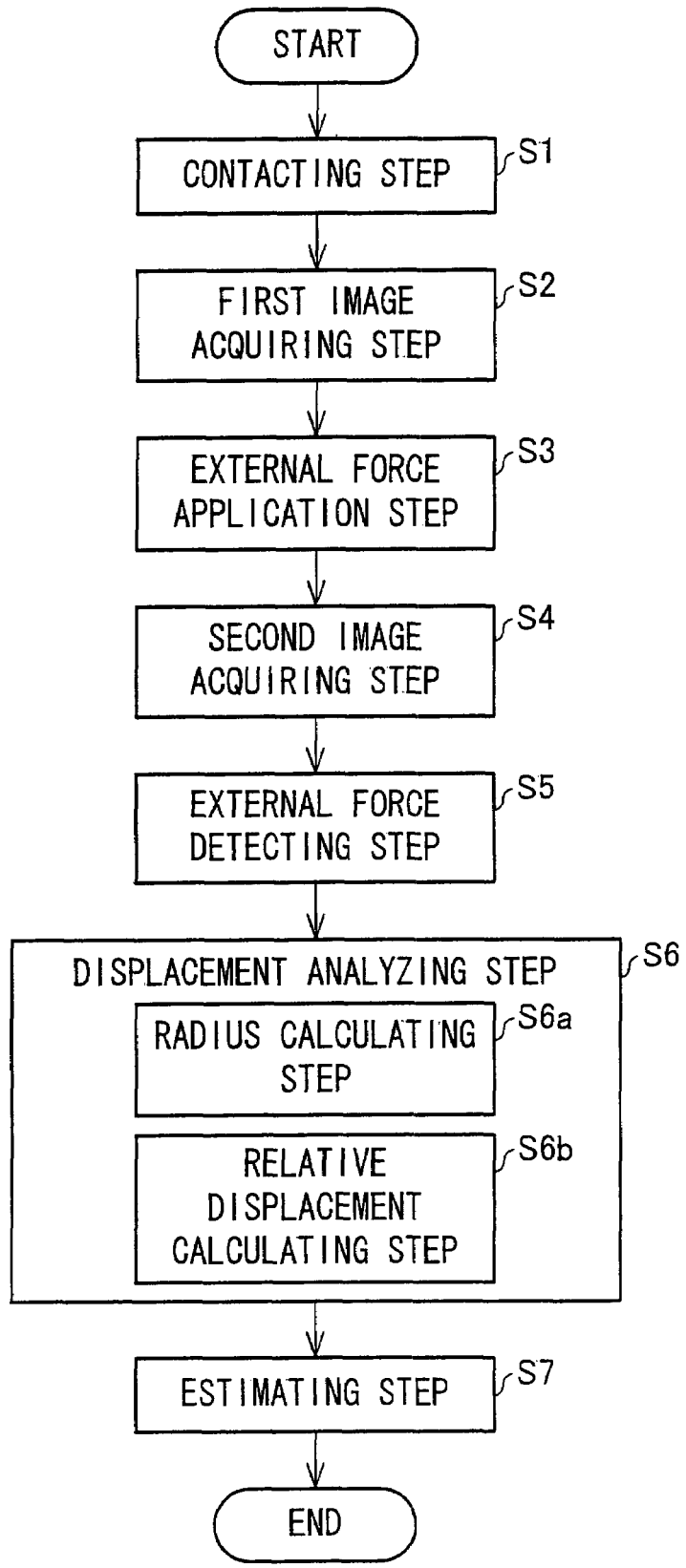
FIG. 6 is a flowchart showing an exemplary operation of detecting a slippage margin, by using a tactile sensor according to the present embodiment.

Next, with reference to a flowchart of FIG. 6, the following describes an exemplary operation to detect the slippage margin by using the tactile sensor 10 of the present embodiment.

As shown in FIG. 6, in Step 1 (Step are hereinafter referred to as S), a user performs a contacting step of causing the elastic member 1a to contact the measurement target 5. Next, in S2, the image acquiring section 2 performs the first image acquiring step of acquiring, as image information, a state of the contact surface 1b of the measurement target 5 and the elastic member 1a in the contacting step S1. In other words, this step is a step of acquiring, as image information, the deformation occurring on the contact surface 1b of the measurement target 5 and the elastic member 1a.

Next, in S3, an external force application step is performed to apply the external force $f_1$ tangential to the contact surface 1b. This step may be performed by the user, or with a use of external force applying means such as a motor or the like. Then, in S4, the image acquiring section 2 performs a second image acquiring step of acquiring as image information a state of deformation occurring on the contact surface 1b of the measurement target 5 and the elastic member 1a, which deformation caused by application of the external force $f_1$ in the external force application step S3. Then, in S5, the external force detecting section 3 performs an external force detecting step of detecting the external force $f_1$ applied in the external force application step S3.

Then, in S6, the deformation analyzing section 7 performs a deformation analyzing step of analyzing deformation information of the contact surface 1b, based on the image information acquired in the first image acquiring step S2 and the second image acquiring step S4. In detail, the deformation analyzing step performed in S6 includes a radius calculating step S6a and a relative displacement calculating step S6b. In other words, in S6a, the radius calculating section 7a performs the radius calculating step to calculate the radius a of the contact surface 1b of the measurement target 5 and the elastic member 1a, based on the image information acquired in the first image acquiring step S2 and/or the second image acquiring step S4. Furthermore, in S6b, the relative displacement calculating section 7b performs the relative displacement calculating step to calculate, based on the image information acquired in the first image acquiring step S2 and the second image acquiring step S4, the relative displacement δ of the contact surface 1b of the measurement target 5 and the elastic member 1a, which displacement caused when the external force $f_1$ is applied tangential to the contact surface 1b.

In S7, the estimating section 8 performs the estimating step of estimating the slippage margin between the measurement target and the elastic member, based on the following: the deformation information of the contact surface 1*b* acquired in the deformation analyzing step S6; the external force $f_1$ detected in the external force detecting step S7; and the object constants G and ν of the elastic member 1*a*. More specifically, the estimating section 8 estimates the slippage margin w by using the calculating formula (the above Formula (5)) of assumed Hertz Contact, based on the radius a and the relative displacement δ of the contact surface which are respectively acquired in the radius calculating step S6*a* and the relative displacement calculating step S6*b* of the deformation analyzing step S6; the external force $f_1$ detected in the external force detecting step S5; and the object constants G and ν of the elastic member 1*a*.

Lastly, the slippage margin calculated by the estimating section 8 is output to an output device 40, which is not illustrated in FIG. 1. For example, the output device 40 may be not only a conventionally known display device such as CRT or a liquid crystal panel, but also a printing device which outputs a hard copy such as a sheet of paper. Further, the sequence of the S5 and S6 may be other way around in the above flowchart.

The external force detecting step S5 is not performed in a case where the tactile sensor does not include the external force detecting section 3. In this case, the calculation can be performed by inputting, via an input device or the like (not shown), the external force $f_1$ applied in the external force application step, as described previously.

As described, in the tactile sensor 10 of the present embodiment, a contact surface of the sensing section of a sensor and the measurement target is acquired in the form of image information. Therefore, the tactile sensor 10 obtains remarkably improved detection accuracy, compared to a pressure-sensing tactile sensor using a conventional stress sensor or the like. Furthermore, with the use of unique calculation algorithm, the slippage margin and the friction factor can be easily but accurately calculated. The elastic member 1*a* only needs to be lightly pushed against the measurement target 5, and an external force only needs to be slightly applied in the tangential direction. It is no longer necessary to actually cause the entire slippage between the measurement target 5 and the elastic member 1*a*.

Embodiment 2

Another arrangement of the tactile sensor according to the present invention is described below. Members having the same functions as those in Embodiment 1 are given the same symbols, and the explanations thereof are omitted. In short, the following description deals with the difference from Embodiment 1.

Embodiment 1 deals with the tactile sensor 10 having the image acquiring section 2 which acquires as the image information a state of the contact surface 1*b* before and after the external force $f_1$ is applied tangential to the contact surface 1*b* of the measurement target 5 and the elastic member 1*a*. In the present embodiment, a tactile sensor has an image acquiring section 2' which does not acquire an image of the contact surface 1*b* of the measurement target 5 and the elastic member 1*a*, before the application of the external force $f_1$ in the tangential direction, but acquires as image information a state of the contact surface 1*b* after the external force $f_1$ is applied.

The image acquiring section 2' is set so that the central position 1*c* of the contact surface 1*b* of the measurement target 5 and the elastic member 1*a* is always in a predetermined position, before the external force $f_1$ is applied tangential to the contact surface 1*b*. Under the condition, the image acquiring section 2' serves as image acquiring means which acquires, in the form of image information, a state of the contact surface 1*b* after the external force $f_1$ is applied tangential to the contact surface 1*b*.

In sum, the image acquiring section 2' does not acquire the image information of the contact surface 1*b* before the external force $f_1$ is applied tangential to the contact surface 1*b* of the measurement target 5 and the elastic member 1*a*. However, if the image acquiring section 2' acquires the image information, the central position 1*c* is always set to be in a predetermined position. As such, the image acquiring section 2' recognizes coordinate information of the central position 1*c* on the contact surface 1*b* before the external force $f_1$ is applied tangential to the contact surface 1*b* of the measurement target 5 and the elastic member 1*a*. Under the condition, the image acquiring section 2' acquires an image showing a state of the contact surface 1*b* after the external force $f_1$ is applied tangential to the contact surface 1*b* of the measurement target 5 and the elastic member 1*a*.

More specifically, for example, the image acquiring section 2' is set so that the center of its optical axis coincides with the central position 1*c* of the contact surface 1*b* of the measurement target 5 and the elastic member 1*a*, before the external force $f_1$ is applied tangential to the contact surface 1*b*. The image acquiring section 2' being so set acquires an image of the contact surface 1*b* after the external force $f_1$ is applied.

In this case, if the elastic member 1*a* is provided on its surface with a diagram which allows the image acquiring section 2' to clearly acquire the central position 1*c* of the contact surface 1*b*, the image acquiring section 2' is easily set so that the optical axis and the diagram coincide each other.

In the above arrangement, the radius calculating section 7*a* calculates the radius a of the contact surface 1*b* from the image information thus acquired. Meanwhile, the relative displacement calculating section 7*b* calculates relative displacement δ, based on the image information and coordinate information of the central position 1*c*. The coordinate information of the central position 1*c* is set in advance in the image acquiring section 2'. Thus, in this case, image information to be acquired is reduced, and therefore the data volume to be processed is reduced. Thus, there is an advantage in that a processing speed is increased.

An exemplary process of estimating a slippage margin with a use of the above-described tactile sensor is described below with reference to a flowchart of FIG. 7.

Figure 7:
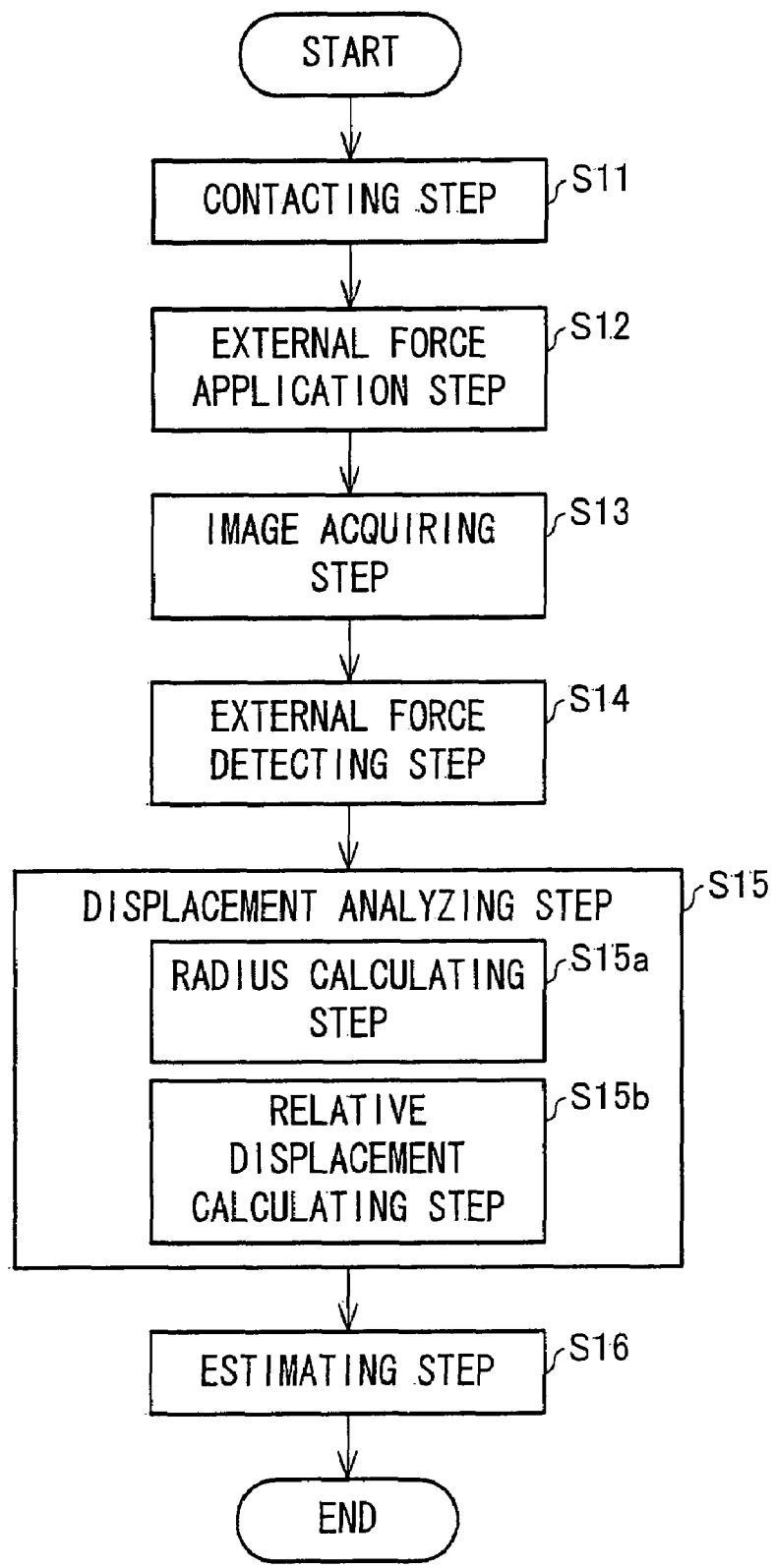
FIG. 7 is a flowchart showing an exemplary operation of detecting a slippage margin, by using a tactile sensor according to another embodiment.

As shown in FIG. 7, in S11, a user performs a contacting step of causing the elastic member 1*a* to contact the measurement target 5. Next, in S12, an external force application step is performed to apply the external force $f_1$ tangential to the contact surface 1*b*. This step may be performed by the user, or with a use of external force applying means such as a motor or the like. Then, in S13, the image acquiring section 2' performs an image acquiring step of acquiring as image information a state of deformation on the contact surface 1*b* of the measurement target 5 and the elastic member 1*a*, which deformation caused by application of the external force $f_1$ in the external force application step S12. Then, in S14, the external force detecting section 3 performs an external force detecting step of detecting the external force $f_1$ applied in the external force application step S12.

Then, in S15, the deformation analyzing section 7 performs a deformation analyzing step of analyzing deformation information of the contact surface 1*b*, based on the image information acquired in the image acquiring step S13 and the pre-set coordinate information of the central position 1*c* (coordinate information of the central position 1*c* in the contact surface 1*b* before the external force $f_1$ is applied). In detail, the deformation analyzing step performed in S15 includes a radius calculating step S15a and a relative displacement calculating step S15b. More specifically, in S15a, the radius calculating section 7a performs the radius calculating step to calculate the radius a of the contact surface 1b of the measurement target 5 and the elastic member 1a, based on the image information acquired in the image acquiring step S13. Furthermore, in S15b, the relative displacement calculating section 7b performs the relative displacement calculating step. In the relative displacement calculating step, the relative displacement δ of the contact surface 1b, caused by the external force $f_1$ applied tangential to the contact surface 1b, is calculated based on the image information acquired in the image acquiring step S13 and the pre-set coordinate information of the central position 1c (coordinate information of the central position 1c in the contact surface 1b before the external force $f_1$ is applied).

The external force detecting step S14 is not performed in a case where the tactile sensor does not include the external force detecting section 3. In this case, the calculation can be performed by inputting, via an input device or the like (not shown), the external force $f_1$ applied in the external force application step, as described previously.

Embodiment 3

Yet another arrangement of the tactile sensor according to the present invention is described below with reference to FIG. 8. Members having the same functions as those in Embodiments 1 and 2 are given the same symbols, and the explanations thereof are omitted. In short, the following description deals with the difference from Embodiments 1 and 2.

Figure 8:
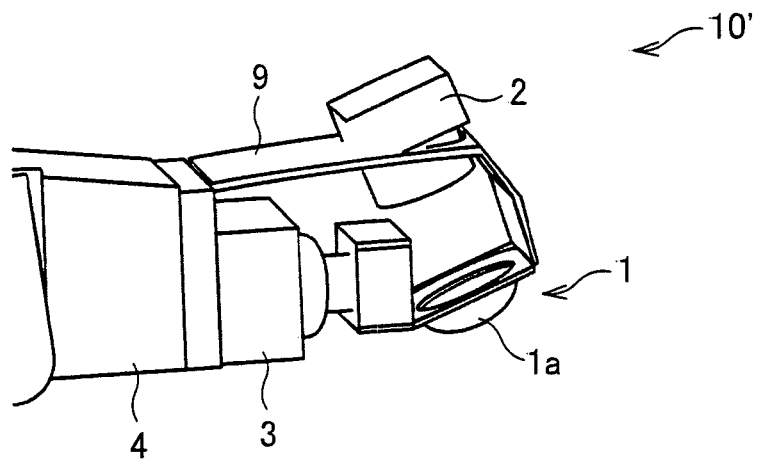
FIG. 8 is a diagram schematically showing a structure of a tactile sensor according to yet another embodiment.

FIG. 8 is a schematic illustration of a tactile sensor of yet another embodiment. As shown in FIG. 8, the tactile sensor 10' of the present embodiment includes: a sensing section 1; an image acquiring section 2; an external force detecting section 3; an information processing unit 4; and a supporting member 9. The sensing section 1 includes a hemispheric elastic member 1a.

The sensing section 1 and the elastic member 1a are transparent. The image acquiring section 2 is provided on a back surface side of the elastic member 1a which side is opposite to a surface of the elastic member 1a which surface contacts the measurement target. The image acquiring section 2 is supported by the supporting member 9. In other words, the image acquiring section 2 is arranged on a side of a surface of the substantially hemispheric elastic member 1a which surface is opposite to the surface having the circumferential portion of the elastic member 1a.

The image acquiring section 2 being thus arranged is able to acquire image information by observing a state of the contact surface of the elastic member 1a and the measurement target, from an inner side with respect to the transparent sensing section 1 and elastic member 1a (i.e., through the transparent sensing section 1 and elastic member 1a).

In this case, since the measurement target needs not to be transparent unlike the case of Embodiment 1, the tactile sensor of the present embodiment can be used in wider range of measurement targets. Furthermore, the image acquiring section 2 is provided on an inner side with respect to the elastic member 1a (on the back surface side of the elastic member 1a which side is opposite to a surface which contacts the measurement target). As such, no object exists on the side where the contact surface exists. Therefore, nothing will physically disturb the elastic member 1a from contacting the measurement target. This allows measurement at a high degree of freedom, and improves the operationality. Further, the tactile sensor, with the image acquiring section 2 being arranged on an inner side with respect to the elastic member 1a as mentioned above, is easily mountable in a friction inspecting device, a gripping device, a robot hand, and the like (described later).

<2. Use of Tactile Sensor According to the Present Invention>

<2-1> Friction Inspecting Device

A tactile sensor according to the present invention is capable of easily but accurately detecting a slippage margin and a friction factor, as described previously. Therefore, the present invention is applicable to various inspecting devices using a tactile sensor. Specifically, a friction inspecting device according to the present invention includes the above-mentioned tactile sensor in a portion that contacts an inspection target (inspection target substance). Specific structures other than that are not particularly limited. Note that the "friction inspecting device" herein is an inspecting device which calculates the friction factor of an inspection target. For example, the inspecting device can be used for evaluating the irregularity of a surface, evaluating surface finish such as painting, polishing, or the like.

With the above structure including the tactile sensor capable of easily but accurately calculating the slippage margin and the friction factor, accurate friction inspection is possible. Further, since it is possible to conduct the inspection in a small space, the above structure is suitable for friction inspection of a curved surface and a portion with small area.

Figure 9:
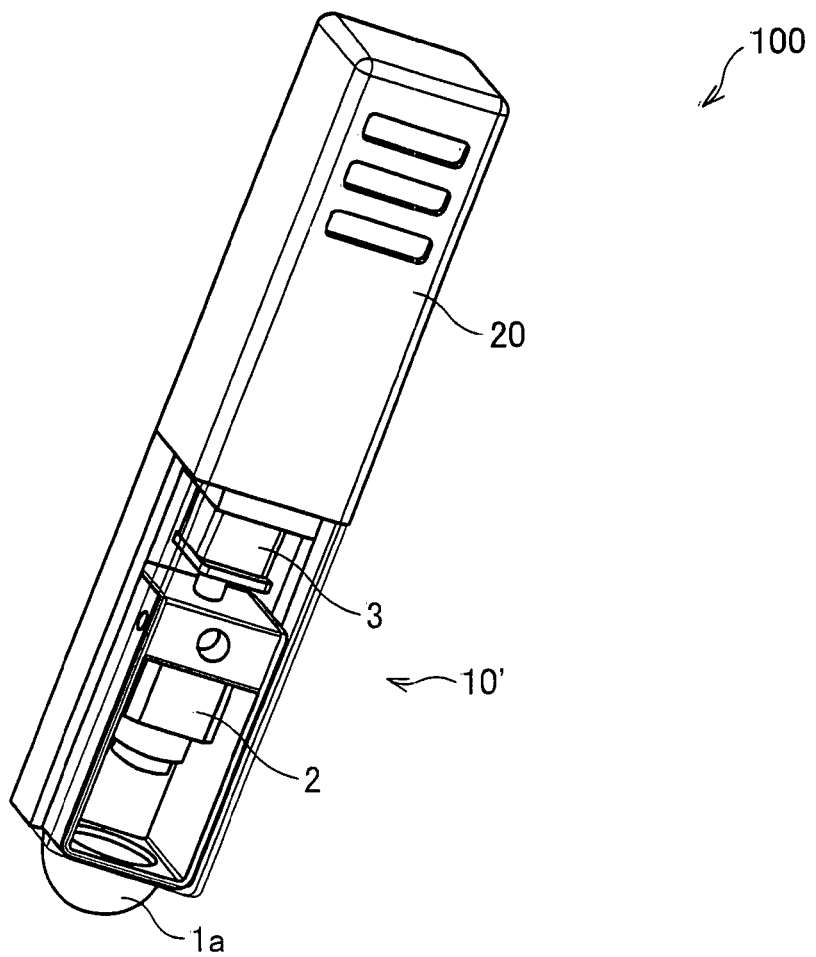
FIG. 9 is a diagram schematically showing a structure of a friction inspecting device according to one embodiment of the present invention.

The following describes an exemplary friction inspecting device of the present invention with reference to a drawing. FIG. 9 is a diagram schematically showing a structure of a friction inspecting device of the present embodiment. As shown in FIG. 9, the friction inspecting device 100 includes: a tactile sensor 10' and a tubiform enclosure 20. The tactile sensor 10' includes: a sensing section 1 having a substantially hemispheric transparent elastic member 1a; an image acquiring section 2; an external force detecting section 3; and an information processing unit 4. The tactile sensor 10' is arranged as described previously, and therefore the explanation thereof is omitted here. Note that the information processing unit 4 is provided inside the tubiform enclosure 20, and is not shown in FIG. 9.

The tubiform enclosure 20 has a shape such that the tactile sensor 10' can be attached thereto. Specific structure of the tubiform enclosure 20 is not particularly limited, provided that it functions as a gripping portion when a user uses the friction inspecting device 100. The present embodiment deals with a case of adopting a parallelepiped tubiform enclosure. However, the tubiform enclosure may be in a cylindrical shape, or in a prism shape. Needless to mention that the width and the length of the tubiform enclosure 20 can be suitably set.

In the friction inspecting device 100, the tactile sensor 10' is provided in the tubiform enclosure 20 in such a manner that the elastic member 1a is in a position to contact the inspection target. In other words, the tactile sensor 10' is mounted in such a manner that the elastic member 1a of the tactile sensor 10' is positioned at the leading end portion of the tubiform enclosure 20.

That is, the friction inspecting device 100 is a so-called pen-shaped friction inspecting device. This structure is advantageous in terms of operationality and portability.

<2-2> Gripping Device

The tactile sensor of the present invention is also suitable for use in a gripping device. Thus, in a gripping device of the present invention, a tactile sensor of the present invention is mounted in a portion that contacts a gripping target (gripping target substance). Note that the "gripping device" herein is a device which holds a gripping target between the gripping device and another object. For example, the gripping device of the present invention encompasses a gripping device, such as a robot hand, which includes a plurality of tactile sensors and holds a gripping target.

Further, the gripping device of the present invention preferably includes control means which performs the following control in holding a gripping target with a use of the mounted tactile sensor. Namely, when the slippage margin of the contact surface of (a) an elastic member in the tactile sensor and (b) the gripping target decreases, the control means controls to increase the grip force. On the contrary, when the slippage margin increases, the control means controls to decrease the grip force. Note that a case where there is variation in the slippage margin of the contact surface of (a) the elastic member of the tactile sensor and (b) the gripping target is, for example, a case where an external force is applied to the gripping target or the elastic member.

Thus, the gripping device of the present invention preferably includes a control section which performs a grip force control in which feedback on the slippage margin is given, and a grip force is controlled according to an updating-rule, based on variation in the slippage margin calculated by the tactile sensor. The following describes the stability in feedback of the slippage margin.

The updating-rule, for use in controlling the grip force on the basis of feedback of the slippage margin, is explained by the following formula (6) using $\Phi$. Thus, even if the friction factor of the contact surface is unknown, the gripping target can be gripped at an arbitrary slippage margin, without a need of estimating the friction factor by actually causing the entire slippage.

$$\dot{f_g} = k(w_d - w(t)) = k(\Phi(t) - \Phi_d) \quad (6)$$

In the formula, k (>0) is a constant feedback gain, $w_d$ (=1−$\Phi_d$) is a targeted value of the slippage margin. Here, note that the friction factor $\mu$ is not necessary. That is, in the Formula (6), the increase/decrease (time differential) of the grip force ($f_g$) is determined by (setting value of the slippage margin–current slippage margin).

By substituting into the above Formula (6) $\Phi=f_1/\mu f_g$ and $f_{gd}=f_1/\mu\Phi_d$, the following Formula (7) is derived.

$$\dot{\varepsilon} = -\alpha \frac{\varepsilon}{\beta - \varepsilon} \quad (7)$$

Here, ($\varepsilon=f_{gd}-f_g$) is an error of the force. $f_{gd}$ is a grip force to realize the targeted slippage margin $\Phi_d$. However, the value of $f_{gd}$ is unknown, because the friction factor $\mu$ is unknown. Further, $\alpha=kf_1/(\mu f_{gd})$ (>0), and $\beta=f_{gd}$. Thus, the Formula (7) is expressed as the following Formula (8).

$$\dot{\varepsilon}(t) = -\beta w \left( -\frac{e^{-\frac{\alpha t + C}{\beta}}}{\beta} \right) \quad (8)$$

w (z) is called Lambert W Function, and satisfies $z=we^w$ (See R. M. Corless, G. H. Gonnet, D. E. G. Hare and D. M. Jeffrey, "On Lambert's W Function." Technical report, Faculty of Mathematics, University of Waterloo, No. 9, pp. 12-22, 1993). W Function is such that w→0 when z→0. Accordingly, where t→∞ in Formula (8), $-e^{-(\alpha_t C)/\beta}/\beta \to 0$, and $\varepsilon$→0. Thus, an error of force relative to the targeted value of an arbitrary slippage margin is converged to 0, and the stability of the above mentioned grip force control is proved.

As described above, the gripping device of the present invention is preferably provided with the control section a control section which performs control, when gripping the gripping target, in such a manner so as to enable continuous gripping of the gripping target while keeping the slippage margin always at a constant value (targeted value of slippage margin) despite variation in the slippage margin between the gripping target and the elastic member.

Figure 10:
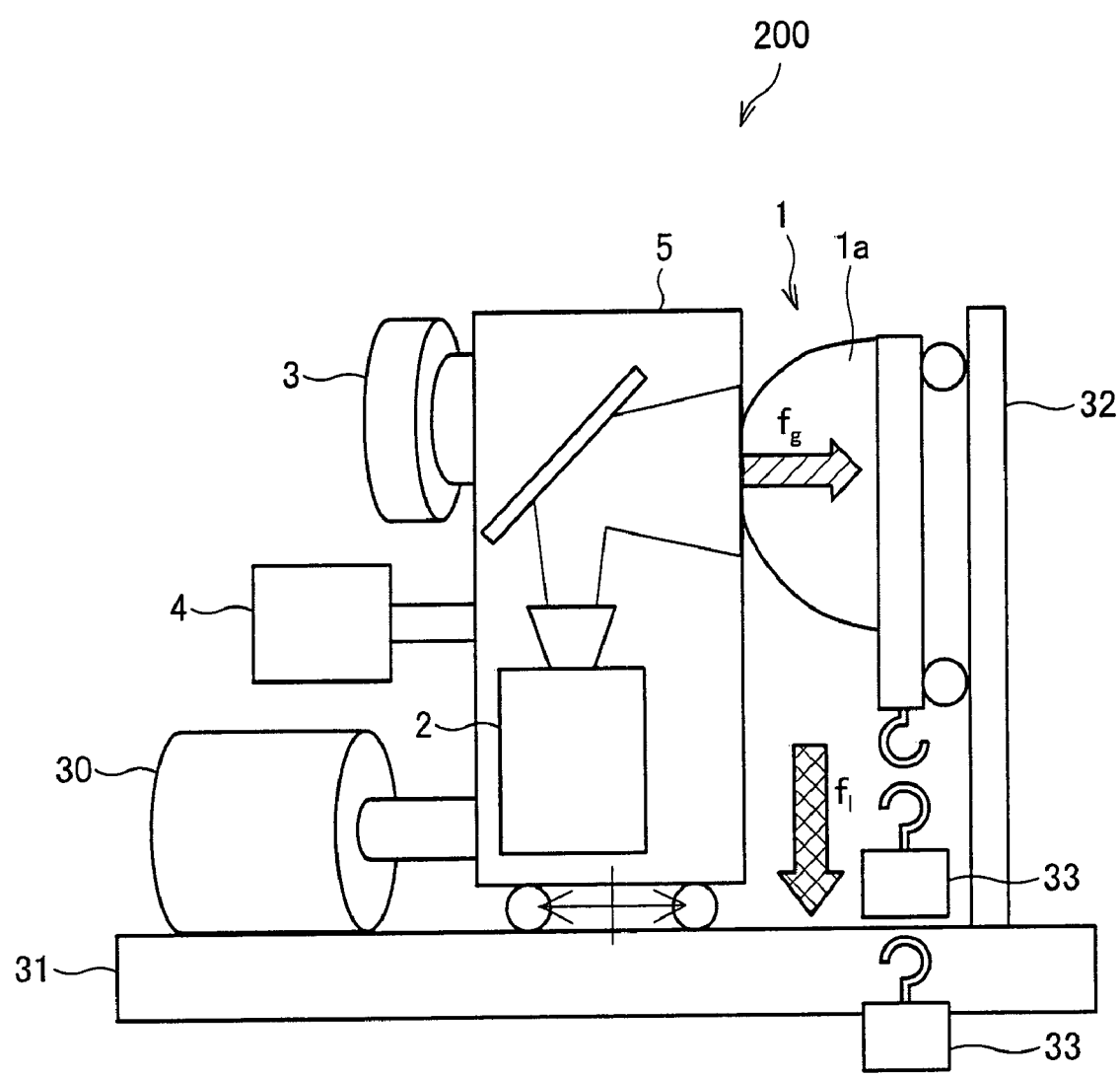
FIG. 10 is a diagram schematically showing a structure of a gripping device according to one embodiment of the present invention.

Next, to confirm the effectiveness of the grip force control, the grip force control was experimented with a use of the gripping device. The results are as follows. Specifically, the experiment was conducted with the use of the gripping device shown in FIG. 10. As shown in FIG. 10, the gripping device 200 was provided with: a tactile sensor 10; a motor 30; a stage 31; a supporting member 32; and weights 33. The tactile sensor 10 was identical in structure with that explained in Embodiment 1, and therefore the explanation thereof is omitted here. Note that, in the present embodiment, the measurement target 5 is the gripping target.

The tactile sensor 10 was placed in such a manner that it was movable on the stage 31. A grip force $f_g$ was applied by the motor 30. Further, the information processing unit 4 was provided with a control section which performs control, when gripping the gripping target, in such a manner as to enable continuous gripping of the gripping target while keeping the slippage margin always at a constant value (targeted value of slippage margin) despite variation in the slippage margin between the gripping target and the elastic member. This control section controlled output of the motor 30.

A transparent acrylic plate was used as the measurement target 5. For the observation of deformation on the contact surface, which was necessary for estimating the slippage margin, a picture of the contact surface of the measurement target 5 and the elastic member 1*a* is taken by a CCD camera from inside of the measurement target 5. By using each of the weights 33, a load (external force) was applied to the elastic member 1*a* in the direction shown by the arrow $f_1$ in FIG. 10.

The feedback gain and the targeted value of the slippage margin were respectively as follows:

feedback gain K=0.3; and targeted value of the slippage margin $\Phi_d$=0.2.

Figure 11A:
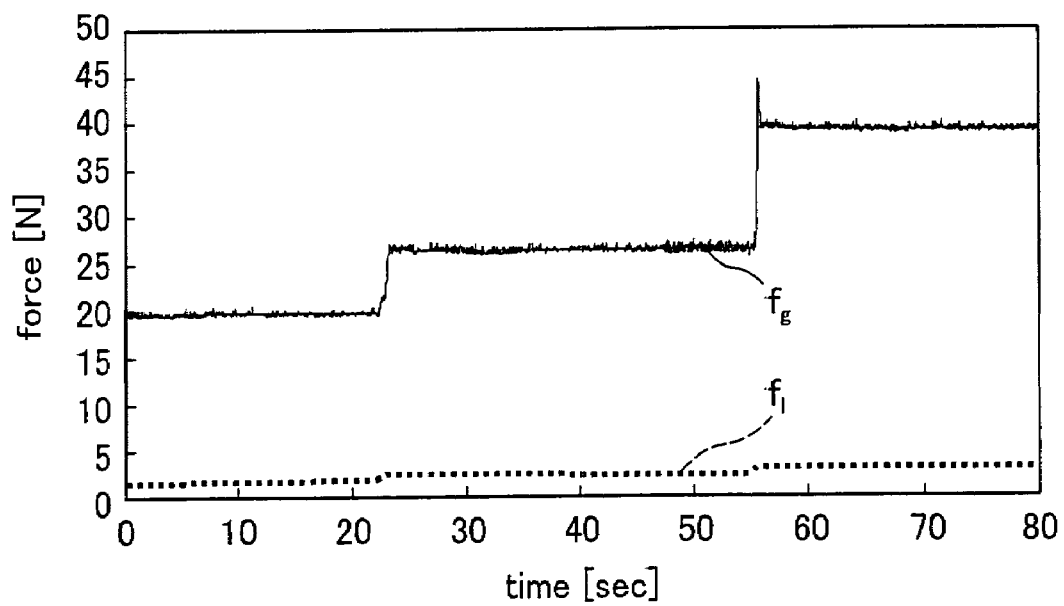
FIG. 11(a) is a diagram showing variation in a grip force $f_g$ and a load $f_1$ when a friction factor $\mu=0.3$, in an experiment of a grip force control using the gripping device of the present embodiment.
Figure 11B:
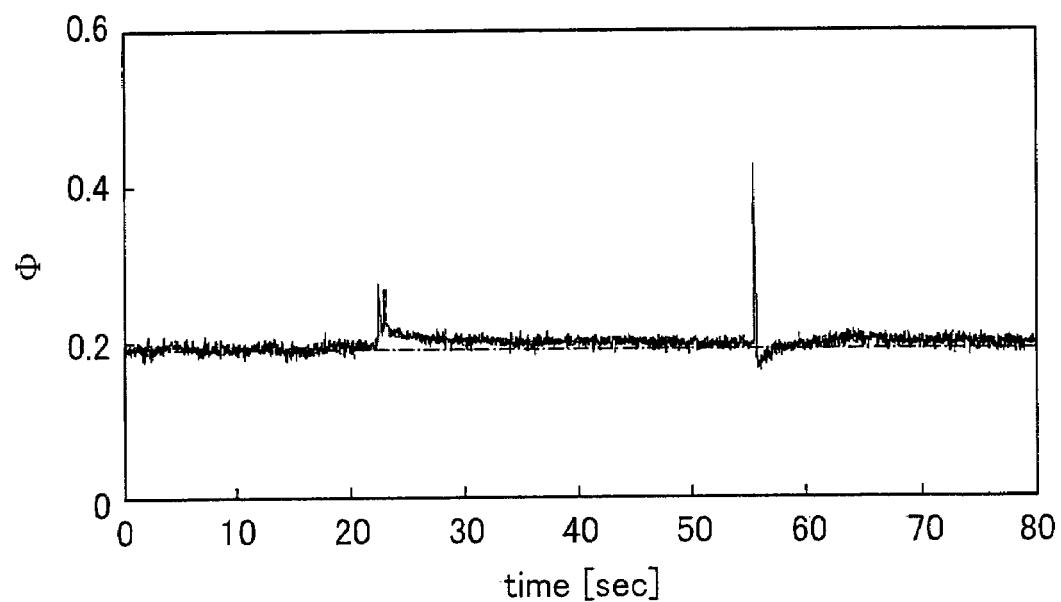
FIG. 11(b) is a diagram showing variation in a slippage margin $\Phi$ when a friction factor $\mu=0.3$, in an experiment of a grip force control using the gripping device of the embodiment.

FIG. 11(*a*) shows variation in the grip force $f_g$ and the load $f_1$, when friction factor $\mu$=0.3. FIG. 11(*b*) shows variation in the slippage margin $\Phi$, when the friction factor $\mu$=0.3. Note that the value of the friction factor $\mu$ was not directly used in the control.

The weight 33 (0.14 (kg)) was added to the elastic member 1*a* one-by-one, when t=23.0 (sec) and when t=57.0 (sec). The added weights 33 caused increase in the load (external force), consequently varying the slippage margin $\Phi$. Feedback on the variation in the slippage margin $\Phi$ is given and reflected to the grip force. Thus, it was confirmed that the gripping target was continuously gripped, while keeping the targeted slippage margin. Although no data is presented here, it was also confirmed that the grip force control was possible through the same method when the friction factor $\mu$ varied. Further, a gripping device having the tactile sensor of FIG. 8 was also controllable in the similar manner.

As described, the gripping device includes the control section (control means) which controls a grip force so as to maintain a predetermined slippage margin when an elastic member of the tactile sensor mounted to the gripping device comes into contact with a gripping target to grip the gripping target, by increasing the grip force when the slippage margin of the contact surface of (A) the elastic member of the tactile sensor and (B) the gripping target decreases, and decreasing the grip force when the slippage margin of the contact surface of (A) the elastic member of the tactile sensor and (B) the gripping target increases. This enables grip force control close to one based on the sense of slippage of a human hand. Thus, a substance can be gripped with a grip force which is not too strong or not too weak, even though the friction factor of the gripped substance is unknown. Note that the control section controls the grip force according to the above Formula (6).

For example, the above mentioned grip force control section is arranged so as to control, based on an estimation result of the slippage margin acquired from the tactile sensor, an operation of means (e.g. motor) for supplying a grip force. Further, the tactile sensor preferably performs sequential (continuous) measurement of the slippage margin, to stably perform the grip force control.

An example of gripping device according to the present invention is a robot hand having on its fingertip the tactile sensor of the present invention. As described previously, the tactile sensor of the present invention is highly accurate in detecting a contact surface, and is capable of being downsized to a mountable size to the fingertip of the robot hand. Accordingly, by mounting in the tactile sensor of the present invention, it is possible to provide a robot hand capable of estimating a slippage margin.

An example of a robot hand to which the tactile sensor of the present invention can be mounted is NAIST-Hand System which has been developed by the inventors. NAIST-Hand System has four fingers each having three degrees of freedom (See J. Ueda, M. Kondo, T. Ogasawara, "Development of NAIST-Hand System for Work Measurement and Skill Generation", Proceedings for The 21st Annual Conference of the Robotics Society of Japan, 3E24, 2003.) At the same time the inventors are also conducting other studies such as: an operation recognition system for direct teaching (See M. Kondo, J. Ueda, Y. Matsumoto, T. Ogasawara, "Development of Object Recognition System for Hyperdactylous Hand", Lecture Note from the 4th Conference of the Society of Instrument and Control Engineers System Integration Division, pp. 269-270, 2003.); and generation of repetitive patterns by nerve oscillator (Y. Kurita, J. Ueda, Y. Matsumoto, T. Ogasawara, "CPG-Based Manipulation: Generation of Rhythmic Finger Gaits from Human Observation", Proc. IEEE Int. Conf. Robotics and Automation pp. 1204-1209, 2004.)

The following briefly explains NAIST-Hand System developed by the inventors, which system is a hyperdactylous-polyarticular robot hand.

A hyperdactylous robot which has humanlike mechanism and freedom degree and make a deft motion has been already developed during the 1980s. However, there were the problems in maintenance and downsizing due to adoption of a wire-driving method. With a recent trend shifting toward a downsized and sophisticated motor, there has been an increasing number of recently-developed robot hands have a mechanism in which motors and gears are mounted in a hand system.

However, there is a limit to downsizing of motors, and a motor capable of generating sufficient torque is not adoptable particularly in a structure in which a drive motor of a PIP joint or DIP joint nearby the fingertip is mounted in a finger.

In view of that, the inventors have developed a hyperductylous polyarticular robot hand in which the above mentioned problems are solved by (i) installing all the drive motors in its palm, and (ii) transmitting the dynamic force via gears and a link structure. More specifically, for a purpose of mounting a PIP joint driving motor in the palm, the inventors developed a mechanism in which 3 pairs of bevel gears (6 gears in total) each pair having two bevel gears of different sizes, are combined at an MP joint (See M. Kondo, J. Ueda, Y. Matsumoto, T. Ogasawara, "Development of Object Recognition System for Hyperdactylous Hand", Lecture Note from the 4th Conference of the Society of Instrument and Control Engineers System Integration Division, pp. 269-270, 2003.). Thus, the PIP joint is driven via the MP joint having two degrees of freedom and a link structure.

Figure 12:
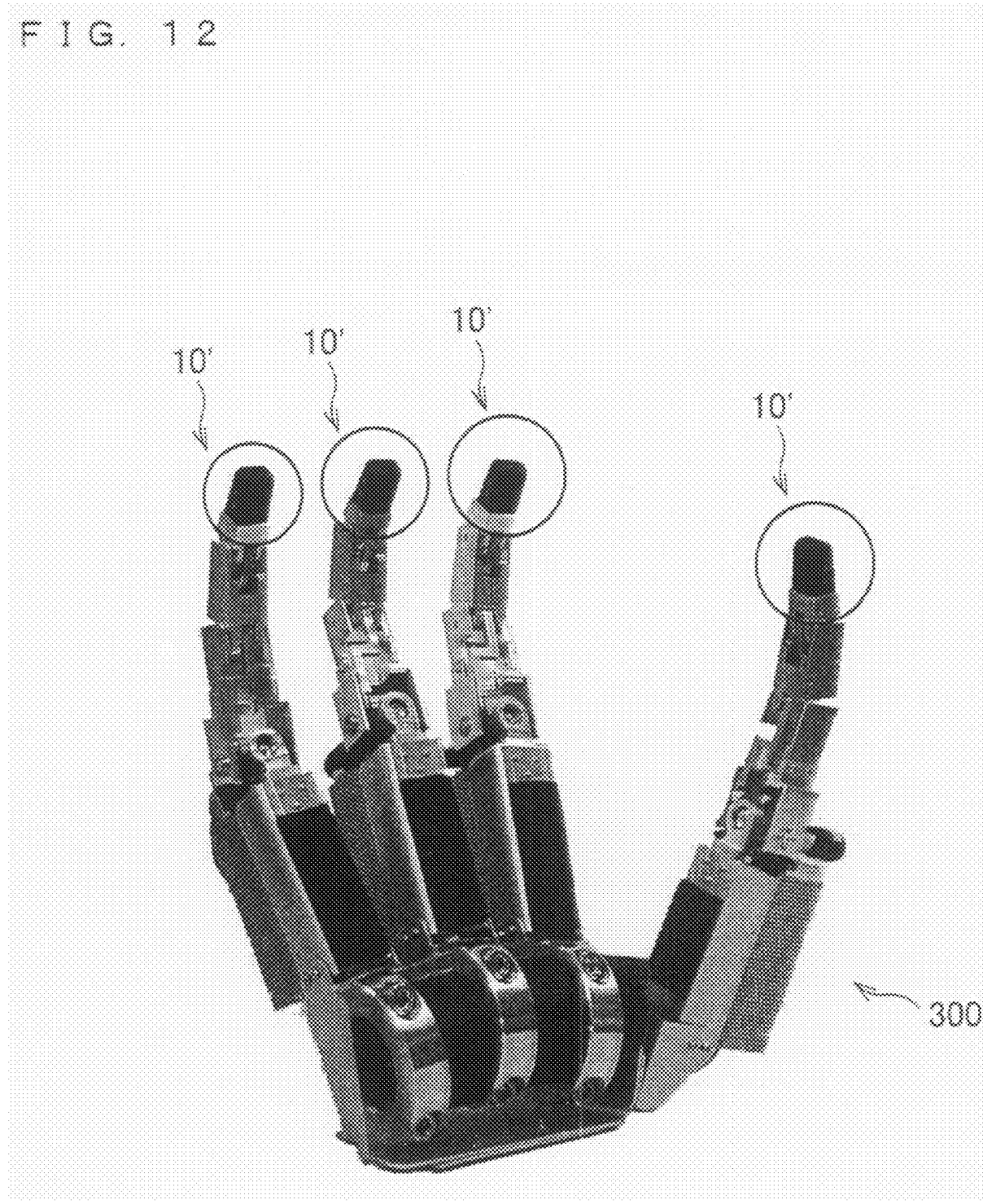
FIG. 12 is a diagram schematically showing a structure of a robot hand according to one embodiment of the present invention.

FIG. 12 shows a hyperdactylous polyarticular robot hand like the above-mentioned NAIST-Hand System having a tactile sensor of the present invention in its fingertips. As shown in FIG. 12, the structure or the like of a robot hand 300 of the present invention is not particularly limited, provided that the tactile sensor 10' is provided in the fingertips of the robot hand 300.

Further, to realize a deft and flexible motion of the robot hand, it is important to control a grip force based on the sense of slippage of human being (See R. S. Johansson and G. Westling, "Roles of glabrous skin receptors and sensorimotor memory in automatic control of precision grip when lifting rougher or more slippery objects", Exp. Brain Res. Vol. 56, pp. 550-564, 1987).

For this reason, it is preferable that the robot hand of the present invention includes a control section which performs the above described grip force control based on feedback of the slippage margin. In this case, for example, the control section controls the operation of drive means (motor) of the robot hand 300, on the basis of an estimation result of slippage margin acquired from the tactile sensor. Specifically, the control section is arranged so as to control a grip force so as to maintain a predetermined slippage margin when an elastic member of the tactile sensor 10' mounted to the robot hand 300 comes into contact with a gripping target to grip the gripping target, by increasing the grip force when the slippage margin of the contact surface of (A) the elastic member of the tactile sensor 10' and (B) the gripping target decreases, and decreasing the grip force when the slippage margin of the contact surface of (A) the elastic member of the tactile sensor 10' and (B) the gripping target increases.

According to the above arrangement, the robot hand has the tactile sensor capable of accurately calculating a slippage margin or a friction factor, and is able to control the grip force so that the slippage margin is always constant. This allows manufacturing of a robot hand which only uses a grip force slightly larger than a minimum grip force to grip an object, even if the friction factor is unknown, as is done by human fingers. In short, the robot hand can operate to grip an object by a not-too strong gripping force, based on the human sense of slippage, while avoiding slippage of the gripped object.

Thus, with the robot hand of the present invention, a complicated handling of an object as is done by a human hand is possible. Therefore, the robot hand of the present invention can be suitably used in, for example, (i) handling a delicate and/or breakable object (e.g., food, medicine, precision machines, and the like) and (ii) a transporting device for these objects. More specifically, the robot hand can be used in handling liquid crystal panels and a transporting device for liquid crystal panels.

Note that the present invention encompasses a tactile sensor including: hemispheric transparent gel having a circumferential portion to contact an object; a characteristic diagram plotted on a surface of the hemispheric transparent gel which surface corresponds to a contact surface; a small camera which measures the contact surface through a plane portion of the hemispheric transparent gel; a frame which supports the hemispheric transparent gel; a force sensor attached to the frame; an image processing algorithm for measuring deformation of the contact surface caused by an occurrence of force between the object and the hemispheric transparent gel; and a calculating algorithm for estimating a slippage margin between the object and the hemispheric transparent gel, based on the measured deformation of the contact surface and a force signal.

The tactile sensor preferably adopts, as the calculating algorithm, a calculating formula of an assumed Hertz Contact. Further, it is preferable that the friction factor between the object and the hemispheric transparent gel be estimated from the slippage margin measured. Further, the slippage margin or the friction factor is preferably estimated by pressing the hemispheric transparent gel serving as a sensing section against the object, and applying a little force that causes no sliding between the object and the gel.

The present invention further encompasses a pen-shaped friction inspecting device having improved portability and operationality, in which device the above mentioned tactile sensor is provided at the leading end of a tubiform enclosure.

The present invention further encompasses a robot hand whose fingertip has the above described tactile sensor, and which is capable of gripping an object at a constant slippage margin without causing an entire slippage between the sensor and the object, by (i) directly estimating the slippage margin; (ii) increasing a grip force if the slippage margin decreases due to application of an external force; and (iii) decreasing a grip force if the slippage margin decreases due to reduction of the external force.

The present invention is not limited to the embodiments above, but may be altered within the scope of the claims. An embodiment based on a proper combination of technical means disclosed in different embodiments is encompassed in the technical scope of the present invention.

Lastly, each block of the information processing unit 4 (particularly the deformation analyzing section 7 and estimating section 8) may be realized in the form of hardware logic, or in the form of software by using a CPU as follows.

Namely, the information processing unit 4 includes: a CPU (Central Processing Unit) which executes commands given by a control program for realizing each function; an ROM (Read Only Memory) storing therein the program; an RAM (Random Access Memory) which runs the program; and a storage device (storage medium) such as memory or the like for storing the program and various data. Further, the object of the present invention is also achieved by: (I) providing the information processing unit 4 with a storage medium storing therein, in a computer-readable manner, program codes (executable format program, intermediate code program, source program) of a control program of the information processing unit 4 which program is the software for realizing the above mentioned functions; and (II) causing a computer (or CPU, MPU) of the information processing unit 4 to read out and execute the program codes stored in the storage medium.

Examples of such a storage medium include a tape, such as a magnetic tape and a cassette tape; a magnetic disk, such as a Floppy Disk® and a hard disk; a disc, such as a CD-ROM/MO/MD/DVD/CD-R; a card, such as an IC card (inclusive of a memory card); and a semiconductor memory, such as a mask ROM, an EPROM (erasable programmable read only memory), an EEPROM (electrically erasable programmable read only memory), or a flash ROM.

Further, the information processing unit 4 may be made connectable to a communication network, and the program codes may be provided via the communication network. A variety of networks can be used as the communication networks. Examples thereof are Internet, intranet, extranet portal, LAN, ISDN, VAN, CATV communication networks, virtual private networks, telephone communication networks, mobile communication networks, and satellite communication networks. Further, a variety of mediums, including a wired line and a radio transmission, can be used as the transmission medium constructing the communication network. Examples of the wired line are an IEEE 1394, USB, a power-line carrier, a cable television circuit, a telephone line, and an ADSL line. Examples of the radio transmission are infrared-ray such as IrDA or a remote control, Bluetooth®, 802.11 radio transmission, HDR, mobile telephone networks, satellite connections, and terrestrial digital networks. The present invention may also be actualized with a carrier wave in which the program code is realized with electronic transmission or a data signal sequence.

INDUSTRIAL APPLICABILITY

According to a tactile sensor of the present invention, it is possible to estimate slippage margin from slight deformation of a contact surface, while causing no entire slippage (actual sliding). Thus, slippage margin and/or friction factor can be simply but accurately estimated. Furthermore, the detection accuracy is higher than a conventional pressure-sensing tactile sensor, because deformation occurring on the contact surface of a measurement target and an elastic member is acquired in the form of image information.

Additionally, with the present invention, measurement is possible if there is a little space for the elastic member of the sensing section to contact the measurement target. Therefore, an accurate measurement can be conducted with respect to an object whose friction factor partially varies and a curved surface or the like.

Further, by using the tactile sensor of the present invention, it is possible to provide a sophisticated gripping device such as a friction inspecting device or a robot hand.

As described, the tactile sensor of the present invention is applicable to wide variety of industry, and can be used in an inspecting device such as a friction inspecting device, a gripping device such as a robot hand, a transferring device or the like.

The invention claimed is:

1. A tactile sensor comprising:
sensing means having an elastic member at a portion which contacts a measurement target;
image acquiring means which acquires as image information a state of the contact surface of (a) the measurement target and (b) the elastic member, before and after application of an external force tangential to the contact surface;
deformation analyzing means which analyzes deformation information of the contact surface, based on the image information acquired by the image acquiring means; and
estimating means which estimates a slippage margin between the measurement target and the elastic member, based on (I) the deformation information of the contact surface, which information acquired by the deformation analyzing means, (II) the external force applied tangential to the contact surface, and (III) an object constant of the elastic member.

2. The tactile sensor according to claim 1, further comprising:
external force detecting means which detects the external force applied tangential to the contact surface.

3. The tactile sensor according to claim 1, wherein
the elastic member is substantially in such a hemispherical shape that its circumferential part contacts the measurement target,
the deformation analyzing means comprises: a radius calculating section which calculates, based on the image information acquired by the image acquiring means, a radius of the contact surface; and a relative displacement calculating section which calculates, based on the image information acquired by the image acquiring means, a relative displacement of the contact surface, which displacement occurs when the external force is applied tangential to the contact surface, and
the estimating means estimates the slippage margin by using a calculating formula of assumed Hertz Contact, based on the radius of the contact surface and the relative displacement, each acquired by the deformation analyzing means, the external force detected by the external force detecting means, and the object constant of the elastic member.

4. The tactile sensor according to claim 1, wherein
a characteristic diagram is formed on a surface of the elastic member, the characteristic diagram allowing the image acquiring means to clearly recognize the central position of the contact surface in a state before the external force is applied tangential to the contact surface.

5. The tactile sensor according to claim 1, wherein
the elastic member is transparent, and
the image acquiring means is provided on a back surface side of the elastic member which side is opposite to a surface which contacts the measurement target.

6. The tactile sensor according to claim 1, further including:
friction factor estimating means which estimates a friction factor between the measurement target and the elastic member, based on the slippage margin estimated by the estimating means.

7. A friction inspecting device comprising a tactile sensor according to claim 1.

8. The friction inspecting device according to claim 7, wherein
the tactile sensor is mounted on a tubiform enclosure so that the elastic member of the tactile sensor is allowed to contact an inspection target.

9. A gripping device comprising a tactile sensor according to claim 1.

10. The gripping device according to claim 9, comprising:
control means which controls a grip force so as to maintain a predetermined slippage margin when an elastic member of the tactile sensor mounted to the gripping device comes into contact with a gripping target to grip the gripping target, by increasing the grip force when the slippage margin of the contact surface of (A) the elastic member of the tactile sensor and (B) the gripping target decreases, and decreasing the grip force when the slippage margin of the contact surface of (A) the elastic member of the tactile sensor and (B) the gripping target increases.

11. The gripping device according to claim 9 wherein
the gripping device is a robot hand.

12. A tactile sensor comprising:
sensing means having an elastic member at a portion which contacts a measurement target;
image acquiring means which is set so that a central position of the contact surface is always in a predetermined position, before the external force is applied tangential to the contact surface of (a) the measurement target and (b) the elastic member, and acquires as image information a state of the contact surface after the external force is applied tangential to the contact surface under a condition where the image acquiring means is set as above;
deformation analyzing means which analyzes deformation information of the contact surface, based on the image information acquired by the image acquiring means; and
estimating means which estimates a slippage margin between the measurement target and the elastic member, based on (I) the deformation information of the contact surface, which information acquired by the deformation analyzing means, (II) the external force applied tangential to the contact surface, and (III) an object constant of the elastic member.

13. A slippage margin measuring method comprising:
a contacting step of causing an elastic member to contact a measurement target;
a first image acquiring step of acquiring as image information a state of a contact surface of (a) the measurement target and (b) the elastic member in the contacting step;
an external force applying step of applying an external force tangential to the contact surface;
a second image acquiring step of acquiring as image information a state of deformation which occurs on the contact surface due to the external force applied in the external force applying step;
a deformation analyzing step of analyzing deformation information of the contact surface, based on the image information acquired in the first image acquiring step and the second image acquiring step; and
an estimating step of estimating a slippage margin between the measurement target and the elastic member, based on (I) the deformation information of the contact surface, which information acquired in the deformation analyzing step, (II) the external force applied in the external force applying step, and (III) an object constant of the elastic member.

14. The slippage margin measuring method according to claim 13, wherein
the elastic member is substantially in such a hemispherical shape that its circumferential part contacts the measurement target,
the deformation analyzing step comprises: a radius calculating step of calculating, based on the image information acquired in the first image acquiring step and/or second image acquiring step, a radius of the contact surface of (a) the measurement target and (b) the elastic member; and a relative displacement calculating step of calculating, based on the image information acquired in the first image acquiring step and/or second image acquiring step, a relative displacement of the contact surface of (a) the measurement target and (b) the elastic member, when a force is applied to the elastic member in a tangential direction to the contact surface of (a) the measurement target and (b) the elastic member, and
the estimating step is a step of estimating the slippage margin by using a calculating formula of assumed Hertz Contact, based on the radius of the contact surface and the relative displacement, each acquired in the deformation analyzing step, the external force applied in the external force applying step, and the object constant of the elastic member.

15. The slippage margin measuring method according to claim 13, further comprising:
an external force detecting step of detecting an external force applied in the external force applying step, wherein in the estimating step, an external force detected in the external force detecting step is used as an external force that has been applied in the external force applying step.

16. The slippage margin measuring method according to claim 13, wherein the elastic member is transparent, and the image acquiring step is a step of acquiring image information by using image acquiring means that is provided on a back surface side of the elastic member which side is opposite to a surface which contacts the measurement target.

17. A slippage margin measuring method comprising:

a contacting step of causing an elastic member to contact a measurement target;

an external force applying step of applying an external force tangential to the contact surface;

an image acquiring step of acquiring as image information a state of deformation which occurs on the contact surface due to the external force applied in the external force applying step;

a deformation analyzing step of analyzing deformation information of the contact surface, based on the image information acquired in the image acquiring step; and an estimating step of estimating a slippage margin between the measurement target and the elastic member, based on (I) the deformation information of the contact surface, which information acquired in the deformation analyzing step, (II) the external force applied in the external force applying step, and (III) an object constant of the elastic member, wherein the image acquiring step is a step of using image acquiring means which is set so that a central position of the contact surface is always in a predetermined position, before the external force is applied tangential to the contact surface of (a) the measurement target and (b) the elastic member, and acquires as image information a state of the contact surface after the external force is applied tangential to the contact surface under a condition where the image acquiring means is set as above.

18. The slippage margin measuring method according to claim 17, wherein the elastic member is substantially in such a hemispherical shape that its circumferential part contacts the measurement target, the deformation analyzing step comprises: a radius calculating step of calculating, based on the image information acquired in the image acquiring step, a radius of the contact surface of (a) the measurement target and (b) the elastic member; and a relative displacement calculating step of calculating, based on (i) the image information acquired in the image acquiring step and (ii) pre-set coordinate information of the central position on the contact surface before the external force is applied, a relative displacement of the contact surface of (a) the measurement target and the (b) the elastic member, when a force is applied to the elastic member in a tangential direction to the contact surface of (a) the measurement target and (b) the elastic member, and the estimating step is a step of estimating the slippage margin by using a calculating formula of assumed Hertz Contact, based on the radius of the contact surface and the relative displacement, each acquired in the deformation analyzing step, the external force applied in the external force applying step, and the object constant of the elastic member.

* * * * *